US008254617B2

(12) United States Patent
Burnett

(10) Patent No.: US 8,254,617 B2
(45) Date of Patent: Aug. 28, 2012

(54) MICROPHONE ARRAY WITH REAR VENTING

(75) Inventor: Gregory C. Burnett, Dodge Center, MN (US)

(73) Assignee: AliphCom, Inc., San Francisco, CA (US)

( * ) Notice: Subject to any disclaimer, the term of this patent is extended or adjusted under 35 U.S.C. 154(b) by 1005 days.

(21) Appl. No.: 12/163,592

(22) Filed: Jun. 27, 2008

(65) Prior Publication Data

US 2009/0003640 A1 Jan. 1, 2009

Related U.S. Application Data

(63) Continuation-in-part of application No. 10/400,282, filed on Mar. 27, 2003, and a continuation-in-part of application No. 10/667,207, filed on Sep. 18, 2003, now Pat. No. 8,019,091, and a continuation-in-part of application No. 11/805,987, filed on May 25, 2007, now abandoned, and a continuation-in-part of application No. 12/139,333, filed on Jun. 13, 2008.

(60) Provisional application No. 60/937,603, filed on Jun. 27, 2007.

(51) Int. Cl.
*H04R 9/08* (2006.01)
*H04B 15/00* (2006.01)
*A61F 11/06* (2006.01)

(52) U.S. Cl. ........ 381/355; 381/71.8; 381/92; 381/94.1; 381/170; 381/375; 704/214; 704/226

(58) Field of Classification Search .................... 381/92, 381/355, 375, 71.8, 94.1, 170; 704/214, 704/226
See application file for complete search history.

(56) References Cited

U.S. PATENT DOCUMENTS

2002/0198705 A1* 12/2002 Burnett .......................... 704/214
2009/0010450 A1* 1/2009 Burnett .......................... 381/92
2009/0010451 A1* 1/2009 Burnett .......................... 381/92
2011/0129101 A1* 6/2011 Hooley .......................... 381/92

* cited by examiner

*Primary Examiner* — Long Tran
(74) *Attorney, Agent, or Firm* — Kokka & Backus, PC

(57) ABSTRACT

Microphone arrays (MAs) are described that position and vent microphones so that performance of a noise suppression system coupled to the microphone array is enhanced. The MA includes at least two physical microphones to receive acoustic signals. The physical microphones make use of a common rear vent (actual or virtual) that samples a common pressure source. The MA includes a physical directional microphone configuration and a virtual directional microphone configuration. By making the input to the rear vents of the microphones (actual or virtual) as similar as possible, the real-world filter to be modeled becomes much simpler to model using an adaptive filter.

17 Claims, 14 Drawing Sheets

1200

1400

MICROPHONE ARRAY WITH REAR VENTING

RELATED APPLICATIONS

This application claims the benefit of U.S. Patent Application No. 60/937,603, filed Jun. 27, 2007.

This application is a continuation in part application of U.S. patent application Ser. Nos. 10/400,282, filed Mar. 27, 2003, 10/667,207, filed Sep. 18, 2003, 11/805,987, filed May 25, 2007, and 12/139,333, filed Jun. 13, 2008.

TECHNICAL FIELD

The disclosure herein relates generally to noise suppression. In particular, this disclosure relates to noise suppression systems, devices, and methods for use in acoustic applications.

BACKGROUND

Conventional adaptive noise suppression algorithms have been around for some time. These conventional algorithms have used two or more microphones to sample both an (unwanted) acoustic noise field and the (desired) speech of a user. The noise relationship between the microphones is then determined using an adaptive filter (such as Least-Mean-Squares as described in Haykin & Widrow, ISBN #0471215708, Wiley, 2002, but any adaptive or stationary system identification algorithm may be used) and that relationship used to filter the noise from the desired signal.

Most conventional noise suppression systems currently in use for speech communication systems are based on a single-microphone spectral subtraction technique first develop in the 1970's and described, for example, by S. F. Boll in "Suppression of Acoustic Noise in Speech using Spectral Subtraction," IEEE Trans. on ASSP, pp. 113-120, 1979. These techniques have been refined over the years, but the basic principles of operation have remained the same. See, for example, U.S. Pat. No. 5,687,243 of McLaughlin, et al., and U.S. Pat. No. 4,811,404 of Vilmur, et al. There have also been several attempts at multi-microphone noise suppression systems, such as those outlined in U.S. Pat. No. 5,406,622 of Silverberg et al. and U.S. Pat. No. 5,463,694 of Bradley et al. Multi-microphone systems have not been very successful for a variety of reasons, the most compelling being poor noise cancellation performance and/or significant speech distortion.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

DETAILED DESCRIPTION

Figure 1:
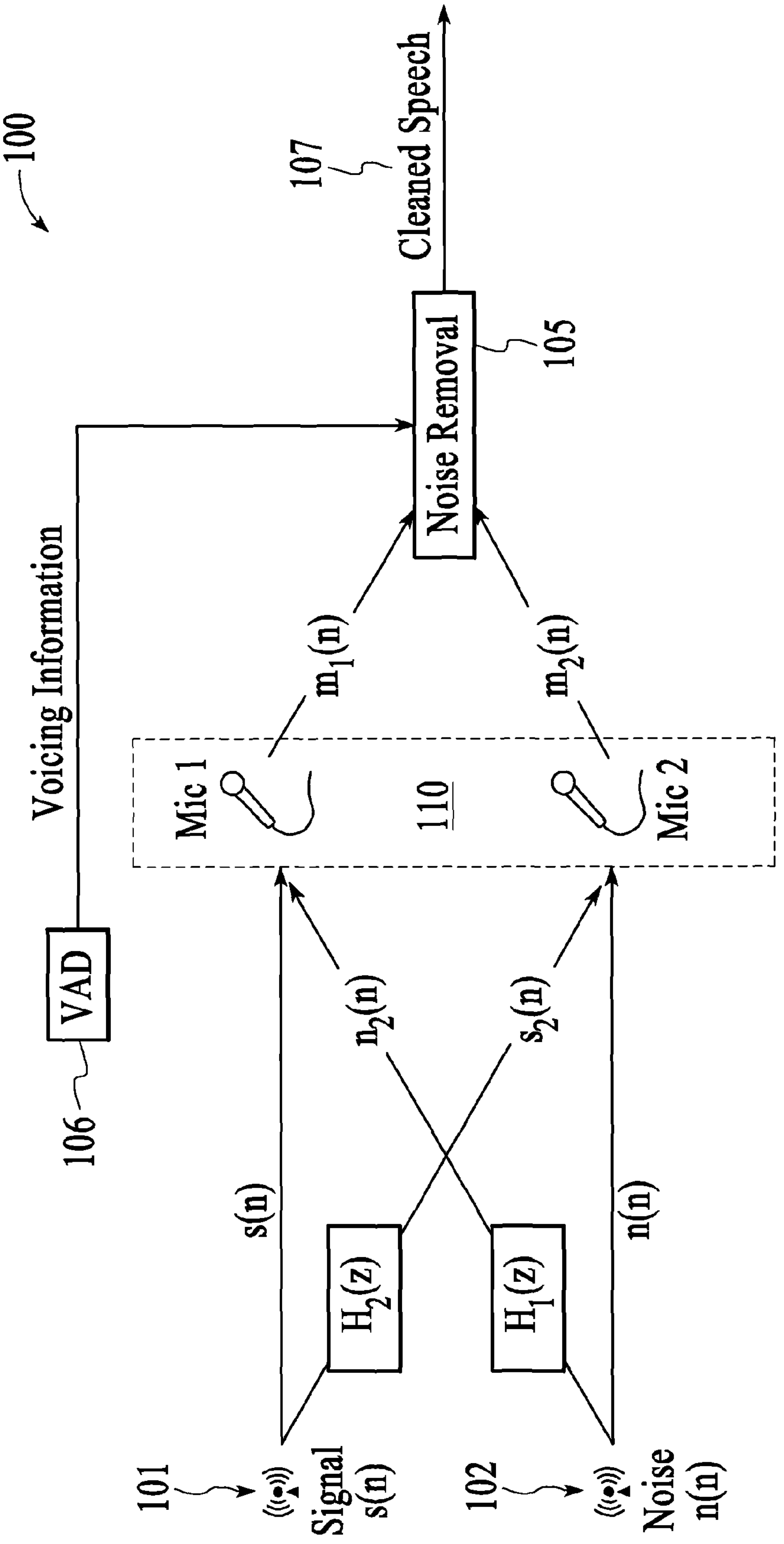
FIG. 1 is a two-microphone adaptive noise suppression system, under an embodiment.

Systems and methods are provided including microphone arrays and associated processing components for use in noise suppression. The systems and methods of an embodiment include systems and methods for noise suppression using one or more of microphone arrays having multiple microphones, an adaptive filter, and/or speech detection devices. More specifically, the systems and methods described herein include microphone arrays (MAs) that position and vent microphones so that performance of a noise suppression system coupled to the microphone array is enhanced.

The MA configuration of an embodiment uses rear vents with the directional microphones, and the rear vents sample a common pressure source. By making the input to the rear vents of directional microphones (actual or virtual) as similar as possible, the real-world filter to be modeled becomes much simpler to model using an adaptive filter. In some cases, the filter collapses to unity, the simplest filter of all. The MA systems and methods described herein have been successfully implemented in the laboratory and in physical systems and provide improved performance over conventional methods. This is accomplished differently for physical directional microphones and virtual directional microphones (VDMs). The theory behind the microphone configuration, and more specific configurations, are described in detail below for both physical and VDMs.

The MAs, in various embodiments, can be used with the Pathfinder system (referred to herein as "Pathfinder") as the adaptive filter system or noise removal. The Pathfinder system, available from AliphCom, San Francisco, Calif., is described in detail in other patents and patent applications referenced herein. Alternatively, any adaptive filter or noise removal algorithm can be used with the MAs in one or more various alternative embodiments or configurations.

The Pathfinder system includes a noise suppression algorithm that uses multiple microphones and a VAD signal to remove undesired noise while preserving the intelligibility and quality of the speech of the user. Pathfinder does this using a configuration including directional microphones and overlapping the noise and speech response of the microphones; that is, one microphone will be more sensitive to speech than the other but they will both have similar noise responses. If the microphones do not have the same or similar noise responses, the denoising performance will be poor. If the microphones have similar speech responses, then devoicing will take place. Therefore, the MAs of an embodiment ensure that the noise response of the microphones is as similar as possible while simultaneously constructing the speech response of the microphones as dissimilar as possible. The technique described herein is effective at removing undesired noise while preserving the intelligibility and quality of the speech of the user.

In the following description, numerous specific details are introduced to provide a thorough understanding of, and enabling description for, embodiments of the microphone array (MA). One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

Unless otherwise specified, the following terms have the corresponding meanings in addition to any meaning or understanding they may convey to one skilled in the art.

The term "speech" means desired speech of the user.

The term "noise" means unwanted environmental acoustic noise.

The term "denoising" means removing unwanted noise from MIC 1, and also refers to the amount of reduction of noise energy in a signal in decibels (dB).

The term "devoicing" means removing/distorting the desired speech from MIC 1.

The term "directional microphone (DM)" means a physical directional microphone that is vented on both sides of the sensing diaphragm.

The term "virtual microphones (VM)" or "virtual directional microphones" means a microphone constructed using two or more omnidirectional microphones and associated signal processing.

The term "MIC 1 (M1)" means a general designation for a microphone that is more sensitive to speech than noise.

The term "MIC 2 (M2)" means a general designation for a microphone that is more sensitive to noise than speech.

The term "null" means a zero or minima in the spatial response of a physical or virtual directional microphone.

The term "$O_1$" means a first physical omnidirectional microphone used to form a microphone array.

The term "$O_2$" means a second physical omnidirectional microphone used to form a microphone array.

The term "$O_3$" means a third physical omnidirectional microphone used to form a microphone array.

The term "$V_1$" means the virtual directional "speech" microphone, which has no nulls.

The term "$V_2$" means the virtual directional "noise" microphone, which has a null for the user's speech.

The term "Voice Activity Detection (VAD) signal" means a signal indicating when user speech is detected.

FIG. 1 is a two-microphone adaptive noise suppression system 100, under an embodiment. The two-microphone system 100 includes the combination of microphone array 110 along with the processing or circuitry components to which the microphone array couples. The processing or circuitry components, some of which are described in detail below, include the noise removal application or component 105 and the VAD sensor 106. The output of the noise removal component is cleaned speech, also referred to as denoised acoustic signals 107.

The microphone array 110 of an embodiment comprises physical microphones MIC 1 and MIC 2, but the embodiment is not so limited, and either of MIC 1 and MIC 2 can be a physical or virtual microphone. Referring to FIG. 1, in analyzing the single noise source 101 and the direct path to the microphones, the total acoustic information coming into MIC 1 is denoted by $m_1(n)$. The total acoustic information coming into MIC 2 is similarly labeled $m_2(n)$. In the z (digital frequency) domain, these are represented as $M_1(z)$ and $M_2(z)$. Then, $$M_1(z)=S(z)+N_2(z)$$

$$M_2(z)=N(z)+S_2(z)$$

with $$N_2(z)=N(z)H_1(z)$$

$$S_2(z)=S(z)H_2(z)$$

so that $$M_1(z)=S(z)+N(z)H_1(z)$$

$$M_2(z)=N(z)+S(z)H_2(z). \qquad \text{Eq. 1}$$

This is the general case for all two-microphone systems. Equation 1 has four unknowns and only two known relationships and therefore cannot be solved explicitly.

However, there is another way to solve for some of the unknowns in Equation 1. The analysis starts with an examination of the case where the speech is not being generated, that is, where a signal from the VAD subsystem 106 (optional) equals zero. In this case, s(n)=S(z)=0, and Equation 1 reduces to $$M_{1N}(z)=N(z)H_1(z)$$

$$M_{2N}(z)=N(z),$$

where the N subscript on the M variables indicate that only noise is being received. This leads to $$M_{1N}(z)=M_{2N}(z)H_1(z) \qquad \text{Eq. 2}$$

$$H_1(z)=\frac{M_{1N}(z)}{M_{2N}(z)}.$$

The function $H_1(z)$ can be calculated using any of the available system identification algorithms and the microphone outputs when the system is certain that only noise is being received. The calculation can be done adaptively, so that the system can react to changes in the noise.

A solution is now available for $H_1(z)$, one of the unknowns in Equation 1. The final unknown, $H_2(z)$, can be determined by using the instances where speech is being produced and the VAD equals one. When this is occurring, but the recent (perhaps less than 1 second) history of the microphones indicate low levels of noise, it can be assumed that n(s)=N(z)~0. Then Equation 1 reduces to $$M_{1S}(z)=S(z)$$

$$M_{2S}(z)=S(z)H_2(z),$$

which in turn leads to $$M_{2S}(z)=M_{1S}(z)H_2(z)$$

$$H_2(z)=\frac{M_{2S}(z)}{M_{1S}(z)},$$

which is the inverse of the $H_1(z)$ calculation. However, it is noted that different inputs are being used (now only the speech is occurring whereas before only the noise was occurring). While calculating $H_2(z)$, the values calculated for $H_1(z)$ are held constant (and vice versa) and it is assumed that the noise level is not high enough to cause errors in the $H_2(z)$ calculation.

After calculating $H_1(z)$ and $H_2(z)$, they are used to remove the noise from the signal. If Equation 1 is rewritten as $$S(z)=M_1(z)-N(z)H_1(z)$$

$$N(z)=M_2(z)-S(z)H_2(z)$$

$$S(z)=M_1(z)-[M_2(z)-S(z)H_2(z)]H_1(z)$$

$$S(z)[1-H_2(z)H_1(z)]=M_1(z)-M_2(z)H_1(z),$$

then N(z) may be substituted as shown to solve for S(z) as $$S(z)=\frac{M_1(z)-M_2(z)H_1(z)}{1-H_1(z)H_2(z)}. \quad \text{Eq. 3}$$

If the transfer functions $H_1(z)$ and $H_2(z)$ can be described with sufficient accuracy, then the noise can be completely removed and the original signal recovered. This remains true without respect to the amplitude or spectral characteristics of the noise. If there is very little or no leakage from the speech source into $M_2$, then $H_2(z)\approx 0$ and Equation 3 reduces to $$S(z)\approx M_1(z)-M_2(z)H_1(z). \quad \text{Eq. 4}$$

Equation 4 is much simpler to implement and is very stable, assuming $H_1(z)$ is stable. However, if significant speech energy is in $M_2(z)$, devoicing can occur. In order to construct a well-performing system and use Equation 4, consideration is given to the following conditions:

R1. Availability of a perfect (or at least very good) VAD in noisy conditions

R2. Sufficiently accurate $H_1(z)$

R3. Very small (ideally zero) $H_2(z)$.

R4. During speech production, $H_1(z)$ cannot change substantially.

R5. During noise, $H_2(z)$ cannot change substantially.

Condition R1 is easy to satisfy if the SNR of the desired speech to the unwanted noise is high enough. "Enough" means different things depending on the method of VAD generation. If a VAD vibration sensor is used, as in Burnett U.S. Pat. No. 7,256,048, accurate VAD in very low SNRs (−10 dB or less) is possible. Acoustic-only methods using information from MIC 1 and MIC 2 can also return accurate VADs, but are limited to SNRs of ~3 dB or greater for adequate performance.

Condition R5 is normally simple to satisfy because for most applications the microphones will not change position with respect to the user's mouth very often or rapidly. In those applications where it may happen (such as hands-free conferencing systems) it can be satisfied by configuring MIC 2 so that $H_2(z)\approx 0$.

Satisfying conditions R2, R3, and R4 are more difficult but are possible given the right combination of microphone output signals. Methods are examined below that have proven to be effective in satisfying the above, resulting in excellent noise suppression performance and minimal speech removal and distortion in an embodiment.

The MA, in various embodiments, can be used with the Pathfinder system as the adaptive filter system or noise removal (element 105 in FIG. 1), as described above. When the MA is used with the Pathfinder system, the Pathfinder system generally provides adaptive noise cancellation by combining the two microphone signals (e.g., MIC 1, MIC 2) by filtering and summing in the time domain. The adaptive filter generally uses the signal received from a first microphone of the MA to remove noise from the speech received from at least one other microphone of the MA, which relies on a slowly varying linear transfer function between the two microphones for sources of noise. Following processing of the two channels of the MA, an output signal is generated in which the noise content is attenuated with respect to the speech content, as described in detail below.

A description follows of the theory supporting the MA with the Pathfinder. While the following description includes reference to two directional microphones, the description can be generalized to any number of microphones.

Pathfinder operates using an adaptive algorithm to continuously update the filter constructed using MIC 1 and MIC 2. In the frequency domain, each microphone's output can be represented as:

$$M_1(z)=F_1(z)-z^{-d_1}B_1(z)$$

$$M_2(z)=F_2(z)-z^{-d_2}B_2(z)$$

where $F_1(z)$ represents the pressure at the front port of MIC 1, $B_1(z)$ the pressure at the back (rear) port, and $z^{-d_1}$ the delay instituted by the microphone. This delay can be realized through port venting and/or microphone construction and/or other ways known to those skilled in the art, including acoustic retarders which slow the acoustic pressure wave. If using omnidirectional microphones to construct virtual directional microphones, these delays can also be realized using delays in DSP. The delays are not required to be integer delays. The filter that is constructed using these outputs is $$H_1(z)=\frac{M_1(z)}{M_2(z)}=\frac{F_1(z)-z^{-d_1}B_1(z)}{F_2(z)-z^{-d_2}B_2(z)}$$

In the case where $B_1(z)$ is not equal to $B_2(z)$, this is an IIR filter. It can become quite complex when multiple microphones are employed. However, if $B_1(z)=B_2(z)$ and $d_1=d_2$, then $$H_1(z)=\frac{F_1(z)-z^{-d_1}B_1(z)}{F_2(z)-z^{-d_1}B_1(z)} \quad (B_1(z)=B_2(z),\ d_1=d_2)$$

The front ports of the two microphones are related to each other by a simple relationship:

$$F_2(z)=Az^{-d_{12}}F_1(z)$$

where A is the difference in amplitude of the noise between the two microphones and $d_{12}$ is the delay between the microphones. Both of these will vary depending on where the acoustic source is located with respect to the microphones. A single noise source is assumed for purposes of this description, but the analysis presented can be generalized to multiple noise sources. For noise, which is assumed to be more than a meter away (in the far field), A is approximately ~1. The delay $d_{12}$ will vary depending on the noise source between $-d_{12max}$ and $+d_{12max}$, where $d_{12max}$ is the maximum delay possible between the two front ports. This maximum delay is a function of the distance between the front vents of the microphones and the speed of sound in air.

The rear ports of the two microphones are related to the front port by a similar relationship:

$$B_1(z)=Bz^{-d_{13}}F_1(z)$$

where B is difference in amplitude of the noise between the two microphones and $d_{FB}$ is the delay between front port 1 and the common back port 3. Both of these will vary depending on where the acoustic source is located with respect to the microphones as shown above with $d_{12}$. The delay $d_{13}$ will vary depending on the noise source between $-d_{13max}$ and $+d_{13max}$, where $d_{13max}$ is the maximum delay possible between front port 1 and the common back port 3. This maximum delay is determined by the path length between front port 1 and the common back port 3—for example, if they are located 3 centimeters (cm) apart, $d_{13max}$ will be $$\begin{aligned} d_{13\max} &= \frac{d}{c} \\ &= \frac{0.03\,m}{345\text{ m/s}} \\ &= 0.87\text{ m sec} \end{aligned}$$

Again, for noise, B is approximately one (1) since the noise sources are assumed to be greater than one (1) meter away from the microphones. Thus, in general, the above equation reduces to:

$$\begin{aligned} H_{1N}(z) &= \frac{F_1(z) - z^{-d_1}Bz^{-d_{13}}F_1(z)}{z^{-d_{12}}F_1(z) - z^{-d_1}Bz^{-d_{23}}F_1(z)} \\ &= \frac{1 - z^{-(d_1+d_{13})}}{z^{-d_{12}} - z^{-(d_1+d_{13})}} \end{aligned}$$

where the "N" denotes that this response is for far-field noise. Since $d_1$ is a characteristic of the microphone, it remains the same for all different noise orientations. Conversely, $d_{13}$ and $d_{12}$ are relative measurements that depend on the location of the noise source with respect to the array.

If d12 goes to or becomes zero (0), then the filter $H_{1N}(z)$ collapses to $$H_{1N}(z) \Rightarrow \frac{1 - z^{-(d_1+d_{13})}}{1 - z^{-(d_1+d_{13})}} = 1 \quad (d_{12} \to 0)$$

and the resulting filter is a simple unity response filter, which is extremely simple to model with an adaptive FIR system. For noise sources perpendicular to the array axis, the distance from the noise source to the front vents will be equal and $d_{12}$ will go to zero. Even for small angles from the perpendicular, $d_{12}$ will be small and the response will still be close to unity. Thus, for many noise locations, the $H_{1N}(z)$ filter can be easily modeled using an adaptive FIR algorithm. This is not the case if the two directional microphones do not have a common rear vent. Even for noise sources away from a line perpendicular to the array axis, the $H_{1N}(z)$ filter is still simpler and more easily modeled using an adaptive FIR filter algorithm and improvements in performance have been observed.

A first approximation made in the description above is that $B_1(z)=B_2(z)$. This approximation means the rear vents are exposed to and have the same response to the same pressure volume. This approximation can be satisfied if the common vented volume is small compared to a wavelength of the sound wave of interest.

A second approximation made in the description above is that $d_1=d_2$. This approximation means the rear port delays for each microphone are the same. This is no problem with physical directional microphones, but must be specified for VDMs. These delays are relative; the front ports can also be delayed if desired, as long as the delay is the same for both microphones.

A third approximation made in the description above is that $F_2(z)$ $F_1(z)$ z-d12. This approximation means the amplitude response of the front vents are about the same and the only difference is a delay. For noise sources greater than one (1) meter away, this is a good approximation, as the amplitude of a sound wave varies as 1/r.

For speech, since it is much closer to the microphones (approximately 1 to 10 cm), A is not unity. The closer to the mouth of the user, the more different from unity A becomes. For example, if MIC 1 is located 8 cm away from the mouth and MIC 2 is located 12 cm away from the mouth, then for speech A would be $$\begin{aligned} A &= \frac{F_2(z)}{F_1(z)} \\ &= \frac{1/12}{1/8} \\ &= 0.67 \end{aligned}$$

This means for speech $H_1(z)$ will be $$H_{1S}(z) = \frac{F_1(z) - z^{-d_1}B_1(z)}{z^{-d_{12}}AF_1(z) - z^{-d_1}B_1(z)}$$

with the "S" denoting the response for near-field speech and $A\neq1$. This does not reduce to a simple FIR approximation and will be harder for the adaptive FIR algorithm to adapt to. This means that the models for the filters $H_{1N}(z)$ and $H_{1S}(z)$ will be very different, thus reducing devoicing. Of course, if a noise source is located close to the microphone, the response will be the similar, which could cause more devoicing. However, unless the noise source is located very near the mouth of the user, a non-unity A and nonzero $d_{12}$ should be enough to limit devoicing.

As an example, the difference in response is next examined for speech and noise when the noise is located behind the microphones. Let $d_1=3$. For speech, let $d_{12}=2$, $A=0.67$, and $B=0.82$. Then $$H_{1S}(z) = \frac{F_1(z) - z^{-d_1} B_1(z)}{z^{-d_{12}} A F_1(z) - z^{-d_1} B_1(z)}$$

$$H_{1S}(z) = \frac{1 - 0.82z^{-3}}{0.67z^{-3} - 0.82z^{-2}}$$

which has a very non-FIR response. For noise located directly opposite the speech, $d_{12}=-2$, A=B=1. Thus the phase of the noise at $F_2$ is two samples ahead of $F_1$. Then $$H_{1N}(z) = \frac{F_1(z) - z^{-3} B_1(z)}{z^2 F_1(z) - z^{-3} B_1(z)} = \frac{z^{-2} - z^{-5}}{1 - z^{-5}}$$

which is much simpler and easily modeled than the speech filter.

Figure 2:
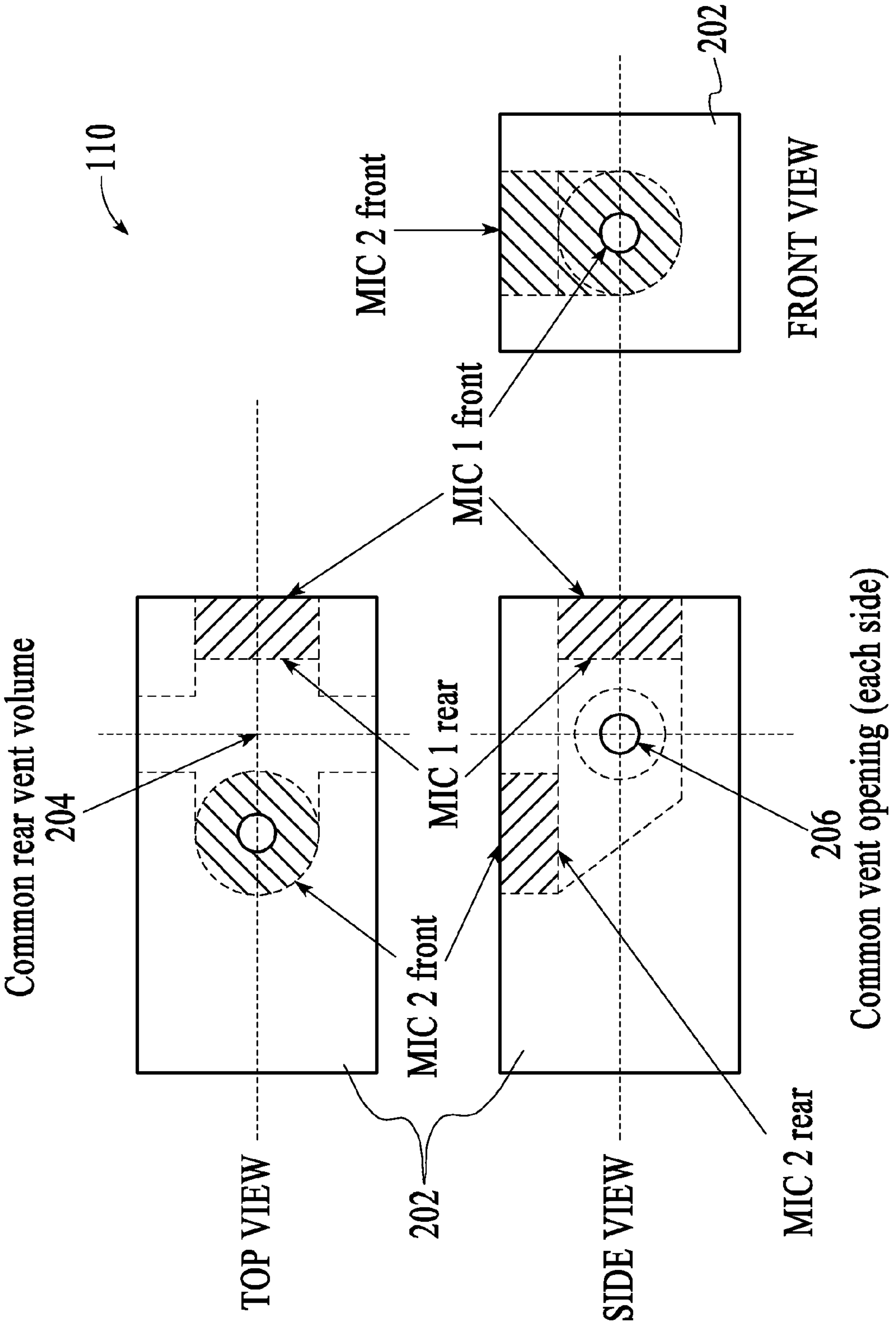
FIG. 2 is a block diagram of a directional microphone array (MA) having a shared-vent configuration, under an embodiment.

The MA configuration of an embodiment implements the technique described above, using directional microphones, by including or constructing a vented volume that is small compared to the wavelength of the acoustic wave of interest and vent the front of the DMs to the outside of the volume and the rear of the DM to the volume itself. FIG. 2 is a block diagram of a microphone array 110 having a shared-vent configuration, under an embodiment. The MA includes a housing 202, a first microphone MIC 1 connected to a first side of the housing, and a second microphone MIC 2 connected to a second side of the housing. The second microphone MIC 2 is positioned approximately orthogonally to the first microphone MIC 1 but is not so limited. The orthogonal relationship between MIC 1 and MIC 2 is shown only as an example, and the positional relationship between MIC 1 and MIC 2 can be any number of relationships (e.g., opposing sides of the housing, etc.). The first and second microphones of an embodiment are directional microphones, but are not so limited.

The housing also includes a vent cavity 204 in an interior region of the housing. The vent cavity 204 forms a common rear port of the first microphone and the second microphone and having a volume that is small relative to a wavelength of acoustic signals received by the first and second microphones. The vent cavity is in an interior region of the housing and positioned behind the first microphone and the second microphone. The vent cavity of an embodiment is a cylindrical cavity having a diameter of approximately 0.125 inch, a length of approximately 0.5 inch, and a volume of approximately 0.0006 cubic inches; however, the vent cavity of alternative embodiments can have any shape and/or any dimensions that provide a volume of approximately 0.0006 cubic inches.

The first microphone and the second microphone sample a common pressure of the vent cavity, and have an equivalent response to the common pressure. The housing of an embodiment includes at least one orifice 206 that connects the vent cavity to an external environment. For example, the housing can include a first orifice in a third side of the housing, where the first orifice connects the vent cavity to an external environment. Similarly, the housing can include, instead of or in addition to the first orifice, a second orifice in a fourth side of the housing, where the second orifice connects the vent cavity to the external environment.

A first rear port of the first microphone and a second rear port of the second microphone are connected to the vent cavity. A first delay of the first rear port is approximately equal to a second delay of the second rear port. Also, a first input to the first rear port is substantially similar to a second input to the second rear port. A first front port of the first microphone and a second front port of the second microphone vent outside the vent cavity.

According to the relationships between the microphones described above, a pressure of the second front port is approximately proportional to a pressure of the first front port multiplied by a difference in amplitude of noise between the first and the second microphone multiplied by a delay between the first and the second microphones. Further, a pressure of the first rear port is approximately proportional to a pressure of the first front port multiplied by a difference in amplitude of noise between the first and the second microphone multiplied by a delay between the first front port and the common rear port.

Generally, physical microphones of the MA of an embodiment are selected and configured so that a first noise response and a first speech response of the first microphone overlaps with a second noise response and a second speech response of the second microphone. This is accomplished by selecting and configuring the microphones such that a first noise response of the first microphone and a second noise response of the second microphone are substantially similar, and a first speech response of the first microphone and a second speech response of the second microphone are substantially dissimilar.

The first microphone and the second microphone of an embodiment are directional microphones. An example MA configuration includes electret directional microphones having a 6 millimeter (mm) diameter, but the embodiment is not so limited. Alternative embodiments can include any type of directional microphone having any number of different sizes and/or configurations. The vent openings for the front of each microphone and the common rear vent volume must be large enough to ensure adequate speech energy at the front and rear of each microphone. A vent opening of approximately 3 mm in diameter has been implemented with good results.

Figure 3:
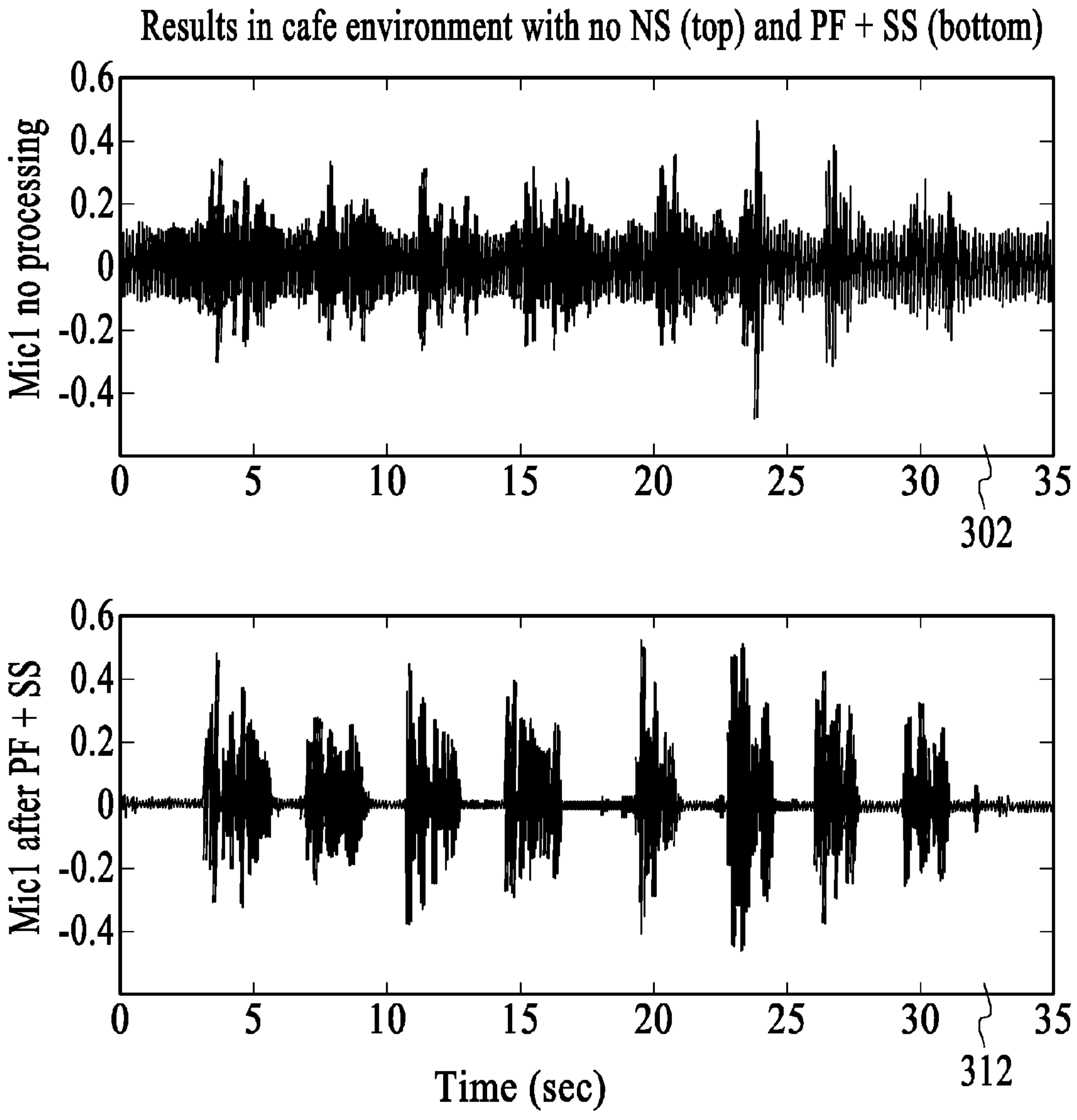
FIG. 3 shows results obtained for a MA having a shared-vent configuration, under an embodiment.

FIG. 3 shows results obtained for a microphone array having a shared-vent configuration, under an embodiment. These experimental results were obtained using the shared-rear-vent configuration described herein using a live subject in a sound room in the presence of complex babble noise. The top plot 302 ("MIC 1 no processing") is the original noisy signal in MIC 1, and the bottom plot 312 ("MIC 1 after PF+SS") the denoised signal (Pathfinder plus spectral subtraction) (under identical or nearly identical conditions) after adaptive Pathfinder denoising of approximately 8 dB and additional single-channel spectral subtraction of approximately 12 dB. Clearly the technique is adept at removing the unwanted noise from the desired signal.

Figure 4:
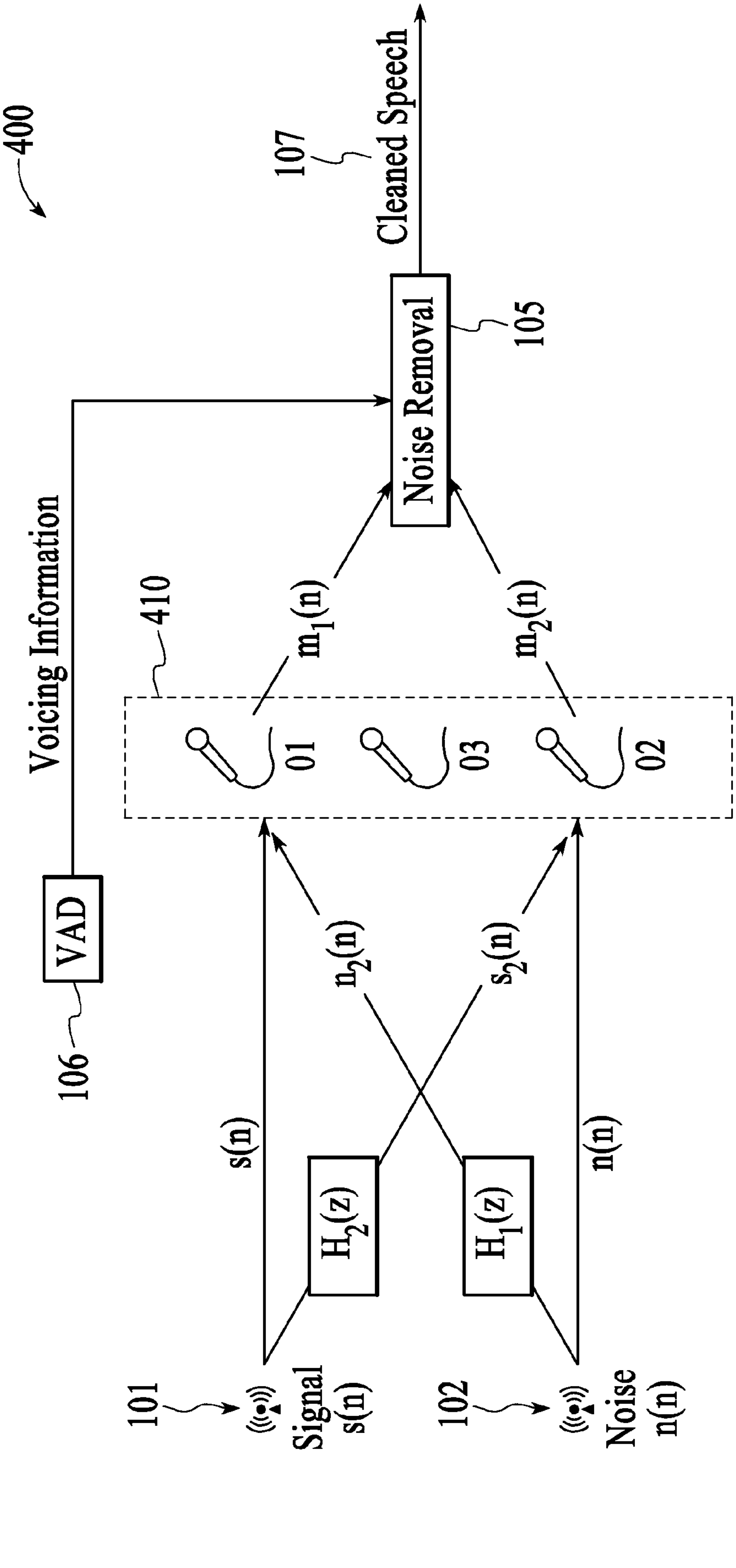
FIG. 4 is a three-microphone adaptive noise suppression system, under an embodiment.

FIG. 4 is a three-microphone adaptive noise suppression system 400, under an embodiment. The three-microphone system 400 includes the combination of microphone array 410 along with the processing or circuitry components to which the microphone array is coupled (described in detail herein, but not shown in this figure). The microphone array 410 includes three physical omnidirectional microphones in a shared-vent configuration in which the omnidirectional microphones form VDMs. The microphone array 410 of an embodiment comprises physical microphones MIC 1, MIC 2 and MIC 3 (correspond to omnidirectional microphones $O_1$, $O_2$, and $O_3$), but the embodiment is not so limited.

Figure 5:
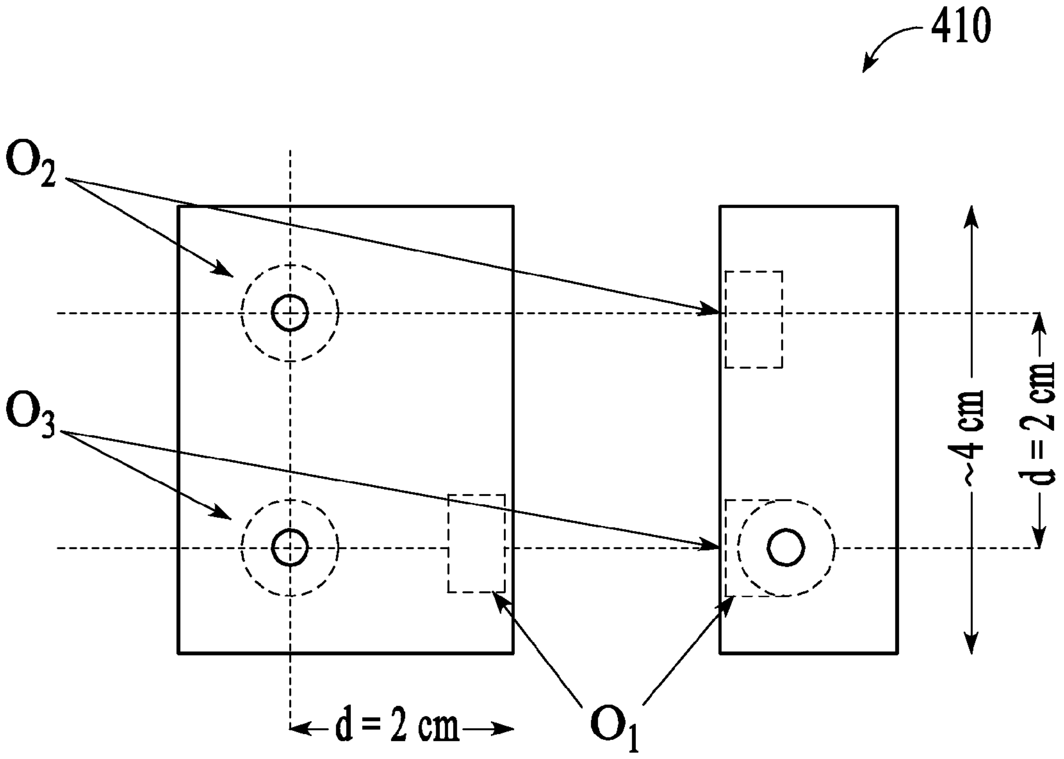
FIG. 5 is a block diagram of the MA in the shared-vent configuration including omnidirectional microphones to form virtual directional microphones (VDMs), under an embodiment.

FIG. 5 is a block diagram of the microphone array 410 in the shared-vent configuration including omnidirectional microphones to form VDMs, under an embodiment. Here, the common "rear vent" is a third omnidirectional microphone situated between the other two microphones. This example embodiment places the first microphone $O_1$ on a first side, and places the second $O_2$ and third $O_3$ microphones on a second side, but the embodiment is not so limited. The relationship between the three microphones is shown only as an example, and the positional relationship between the three microphones can be any number of relationships (e.g., all microphones on a same side of the housing, each microphone on a different side of the housing, any combination of two microphones on a same side, etc.). MIC 1 and MIC 2 (as defined above) can be defined as:

$$M_1 - O_1 - O_3 z^{-dt}$$

$$M_2 = O_2 - O_3 z^{-dt}$$

Here the distances "d" between the microphones are equal but the embodiment is not so limited. The delay time "dt" is the time it takes for the sound to travel the distance "d". In this embodiment, assuming a temperature of 20 Celsius, that time would be about $5.83 \times 10^{-5}$ seconds. The above assumes that all three omnidirectional microphones have been calibrated so that their response to an identical source is the same, but this is not limiting as calibration techniques are well known to those in the art. Different combinations of two or more microphones are possible, but the virtual "rear vents" are as similar as possible to derive full benefit from this configuration. The MA configuration of an embodiment dedicates a single microphone (in this case $O_3$) to be the rear "vent" for both VDMs.

Figure 6:
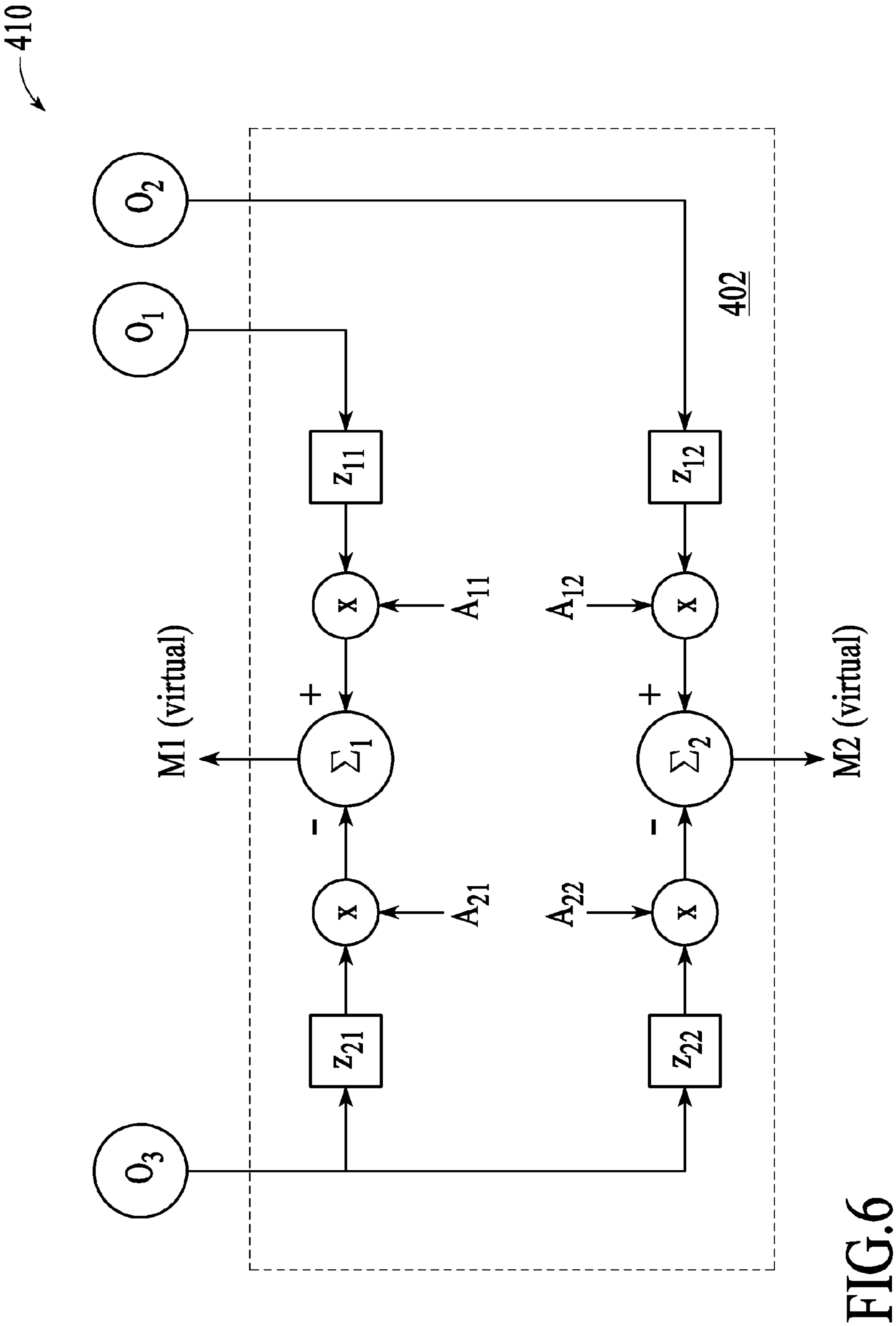
FIG. 6 is a block diagram for a MA including three physical omnidirectional microphones configured to form two virtual microphones $M_1$ and $M_2$, under an embodiment.

As an example, FIG. 6 is a block diagram for a MA 410 including three physical microphones configured to form two virtual microphones $M_1$ and $M_2$, under an embodiment. The MA includes two first order gradient microphones $M_1$ and $M_2$ formed using the outputs of three microphones or elements $O_1$, $O_2$ and $O_3$, under an embodiment. The MA of an embodiment includes three physical microphones that are omnidirectional microphones, as described above. The output from each physical microphone is coupled to a processing component 602, or circuitry, and the processing component 602 outputs signals representing or corresponding to the virtual microphones $M_1$ and $M_2$.

In this example system 410, the output of physical microphone $O_1$ is coupled to a first processing path of processing component 602 that includes application of a first delay $z_{11}$ and a first gain $A_{11}$. The output of physical microphone $O_2$ is coupled to a second processing path of processing component 602 that includes application of a second delay $z_{12}$ and a second gain $A_{12}$. The output of physical microphone $O_3$ is coupled to a third processing path of the processing component 602 that includes application of a third delay $z_{21}$ and a third gain $A_{21}$ and a fourth processing path that includes application of a fourth delay $z_{22}$ and a fourth gain $A_{22}$. The output of the first and third processing paths is summed to form virtual microphone $M_1$, and the output of the second and fourth processing paths is summed to form virtual microphone $M_2$.

As described in detail below, varying the magnitude and sign of the delays and gains of the processing paths leads to a wide variety of virtual microphones (VMs), also referred to herein as virtual directional microphones, can be realized. While the processing component 602 described in this example includes four processing paths generating two virtual microphones or microphone signals, the embodiment is not so limited.

Figure 7:
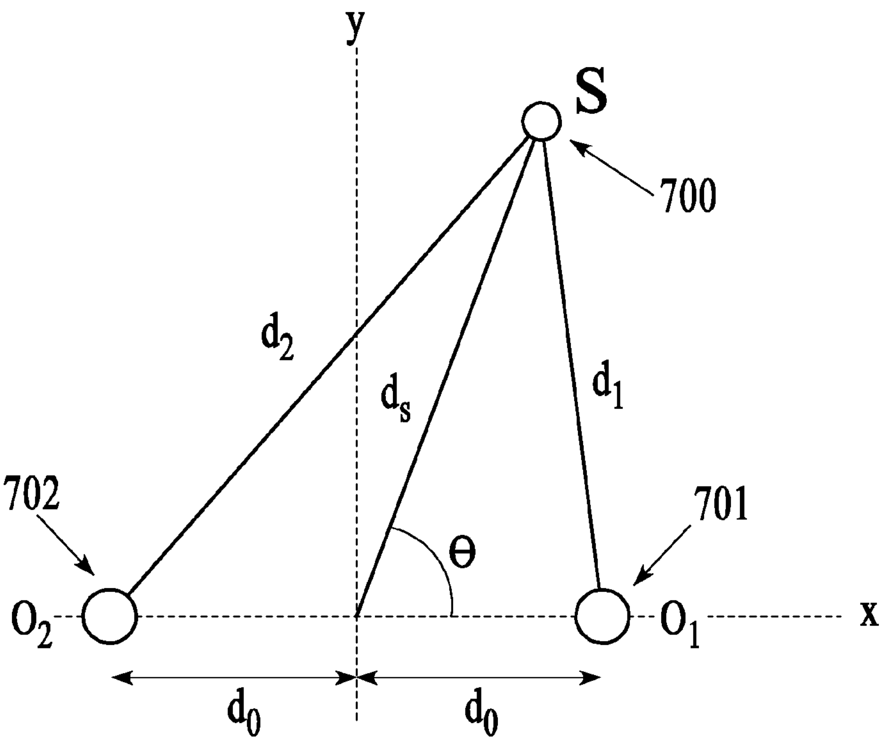
FIG. 7 is a generalized two-microphone array including an array and speech source S configuration, under an embodiment.
Figure 8:
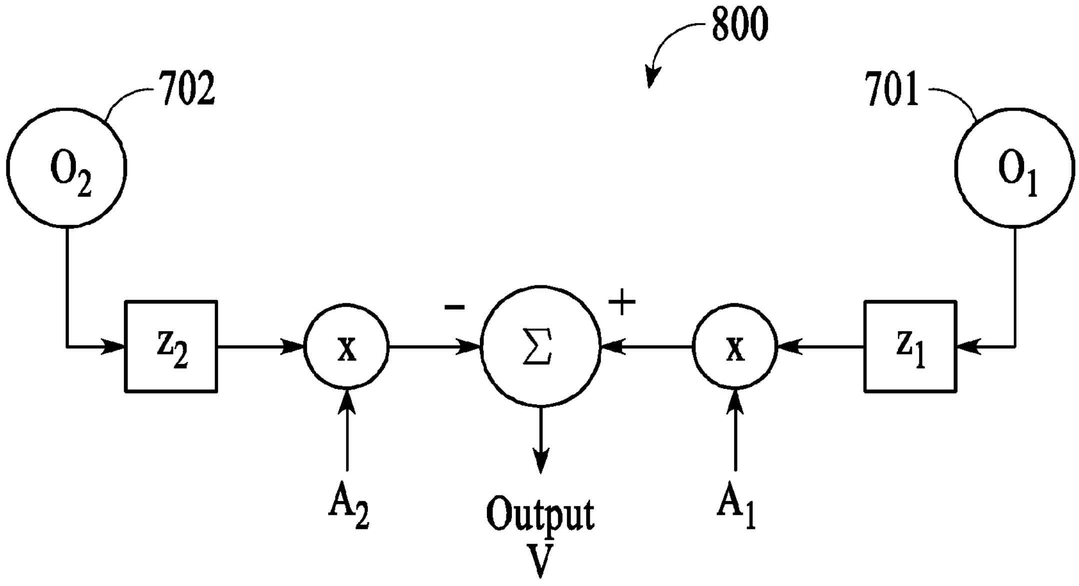
FIG. 8 is a system for generating a first order gradient microphone V using two omnidirectional elements $O_1$ and $O_2$, under an embodiment.

A generalized description follows of formation of virtual microphones or virtual microphone arrays from physical microphones or physical microphone arrays. FIG. 7 is a generalized two-microphone array (MA) including an array 701/702 and speech source S configuration, under an embodiment. FIG. 8 is a system 800 for generating or producing a first order gradient microphone V using two omnidirectional elements $O_1$ and $O_2$, under an embodiment. The generalized array includes two physical microphones 701 and 702 (e.g., omnidirectional microphones) placed a distance $2d_0$ apart and a speech source 700 located a distance $d_s$ away at an angle of θ. This array is axially symmetric (at least in free space), so no other angle is needed. The output from each microphone 701 and 702 can be delayed ($z_1$ and $z_2$), multiplied by a gain ($A_1$ and $A_2$), and then summed with the other as described above and as demonstrated in FIG. 8. The output of the array is or forms at least one virtual microphone, as described in detail herein. This operation can be over any frequency range desired. By varying the magnitude and sign of the delays and gains, a wide variety of virtual microphones (VMs), also referred to herein as virtual directional microphones, can be realized. There are other methods known to those skilled in the art for constructing VMs but this is a common one and will be used in the enablement below.

Figure 9:
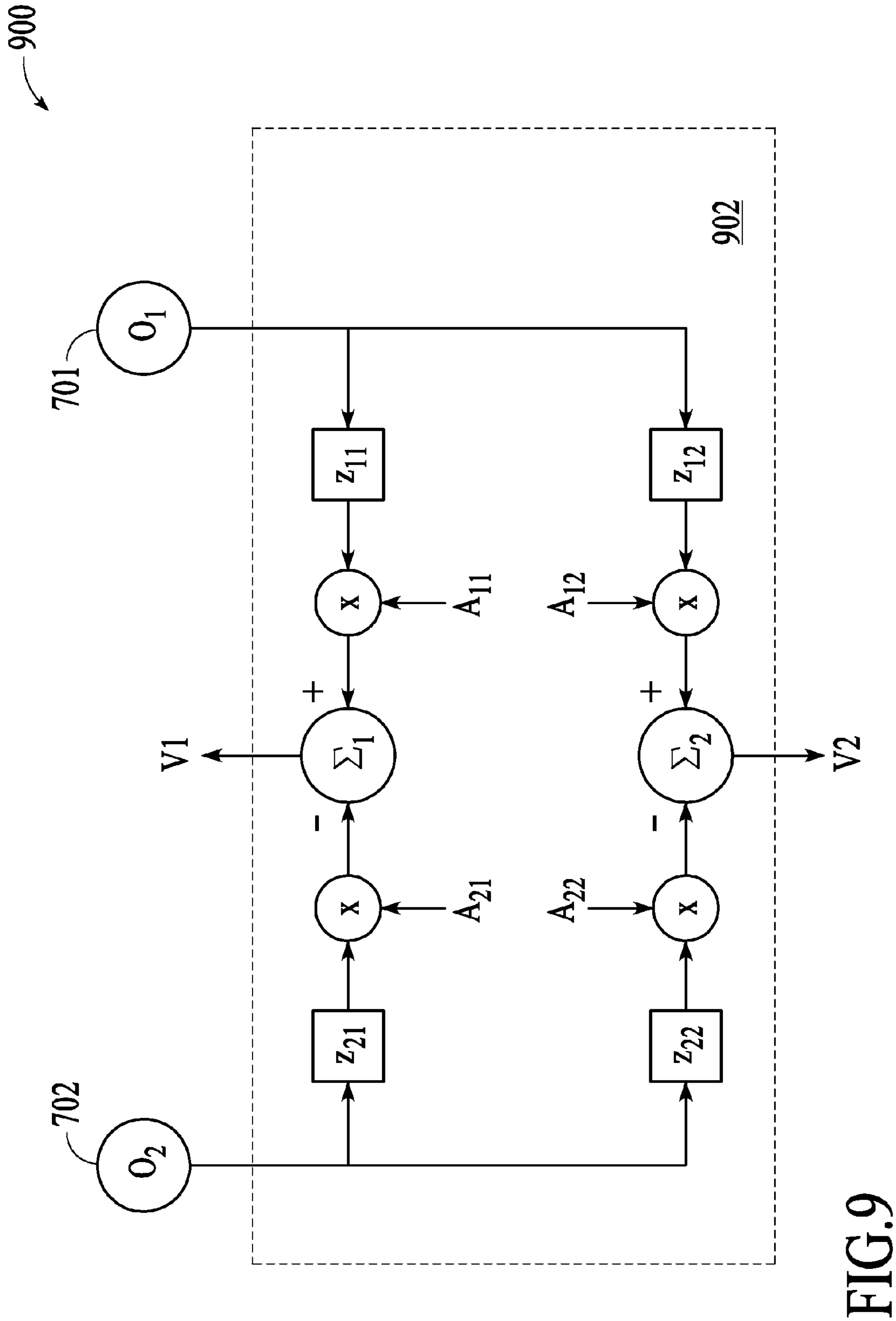
FIG. 9 is a block diagram for a MA including two physical microphones configured to form two virtual microphones $V_1$ and $V_2$, under an embodiment.

As an example, FIG. 9 is a block diagram for a MA 900 including two physical microphones configured to form two virtual microphones $V_1$ and $V_2$, under an embodiment. The MA includes two first order gradient microphones $V_1$ and $V_2$ formed using the outputs of two microphones or elements $O_1$ and $O_2$ (701 and 702), under an embodiment. The MA of an embodiment includes two physical microphones 701 and 702 that are omnidirectional microphones, as described herein. The output from each microphone is coupled to a processing component 902, or circuitry, and the processing component outputs signals representing or corresponding to the virtual microphones $V_1$ and $V_2$.

In this example system 900, the output of physical microphone 701 is coupled to processing component 702 that includes a first processing path that includes application of a first delay $z_{11}$ and a first gain $A_{11}$ and a second processing path that includes application of a second delay $z_{12}$ and a second gain $A_{12}$. The output of physical microphone 702 is coupled to a third processing path of the processing component 902 that includes application of a third delay $z_{21}$ and a third gain $A_{21}$ and a fourth processing path that includes application of a fourth delay $z_{22}$ and a fourth gain $A_{22}$. The output of the first and third processing paths is summed to form virtual microphone $V_1$, and the output of the second and fourth processing paths is summed to form virtual microphone $V_2$.

Figure 10:
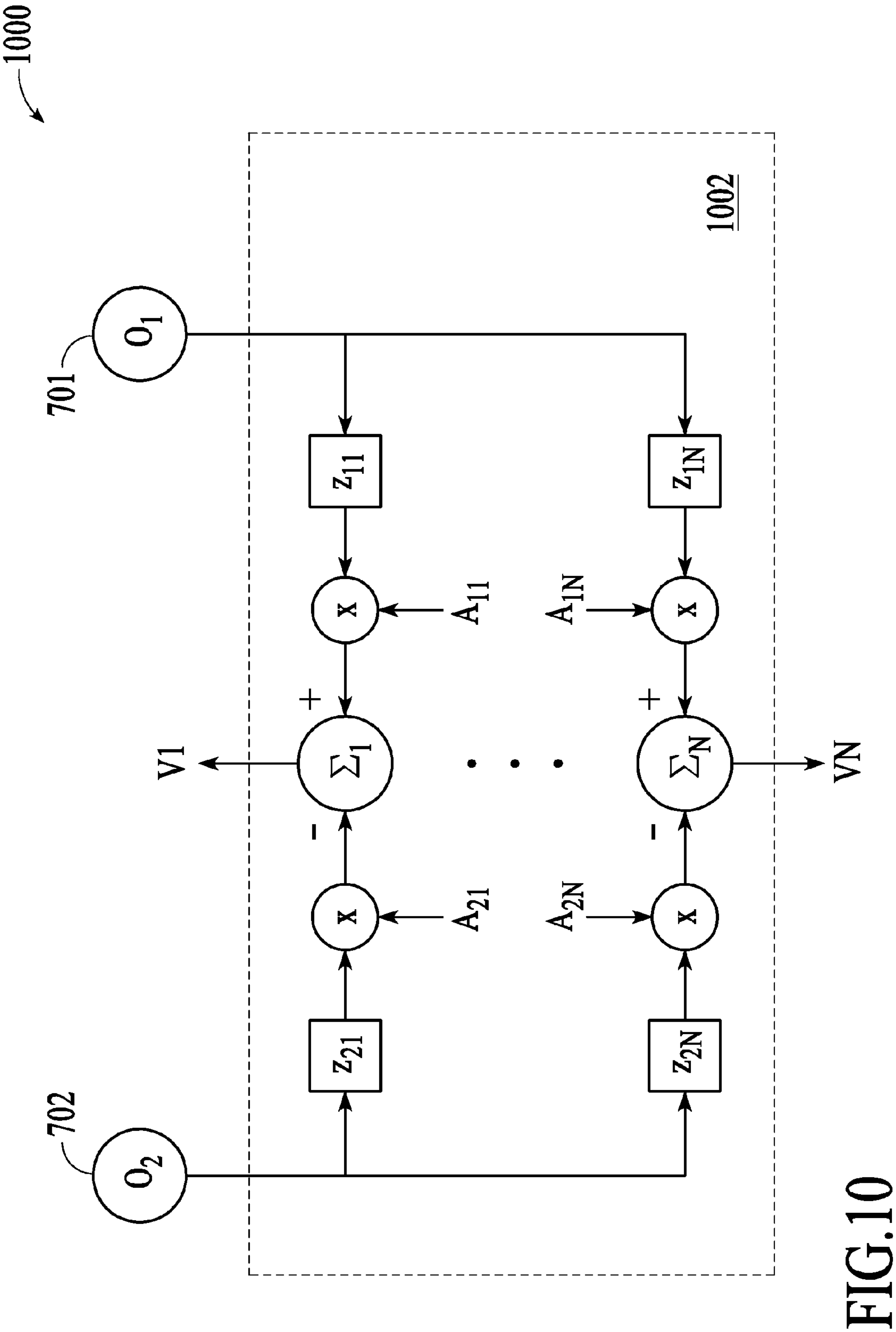
FIG. 10 is a block diagram for a MA including two physical microphones configured to form N virtual microphones $V_1$ through $V_N$, where N is any number greater than one, under an embodiment.

As described in detail below, varying the magnitude and sign of the delays and gains of the processing paths leads to a wide variety of virtual microphones (VMs), also referred to herein as virtual directional microphones, can be realized. While the processing component 902 described in this example includes four processing paths generating two virtual microphones or microphone signals, the embodiment is not so limited. For example, FIG. 10 is a block diagram for a MA 1000 including two physical microphones configured to form N virtual microphones $V_1$ through $V_N$, where N is any number greater than one, under an embodiment. Thus, the MA can include a processing component 1002 having any number of processing paths as appropriate to form a number N of virtual microphones.

The MA of an embodiment can be coupled or connected to one or more remote devices. In a system configuration, the MA outputs signals to the remote devices. The remote devices include, but are not limited to, at least one of cellular telephones, satellite telephones, portable telephones, wireline telephones, Internet telephones, wireless transceivers, wireless communication radios, personal digital assistants (PDAs), personal computers (PCs), headset devices, headworn devices, and earpieces.

Furthermore, the MA of an embodiment can be a component or subsystem integrated with a host device. In this system configuration, the MA outputs signals to components or subsystems of the host device. The host device includes, but is not limited to, at least one of cellular telephones, satellite telephones, portable telephones, wireline telephones, Internet telephones, wireless transceivers, wireless communication radios, personal digital assistants (PDAs), personal computers (PCs), headset devices, head-worn devices, and earpieces.

Figure 11:
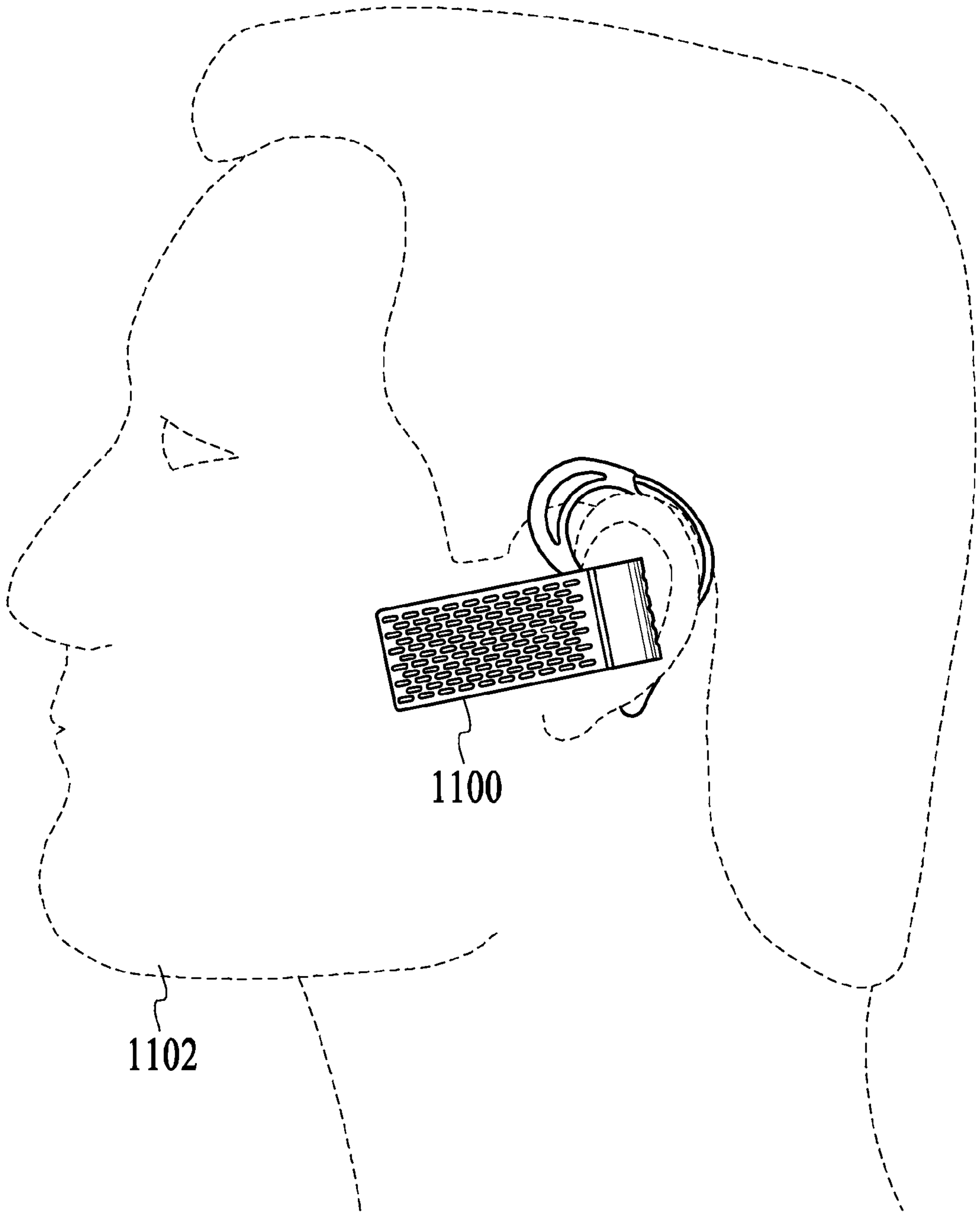
FIG. 11 is an example of a headset or head-worn device that includes the MA, under an embodiment.

As an example, FIG. 11 is an example of a headset or head-worn device 1100 that includes the MA, as described herein, under an embodiment. The headset 1100 of an embodiment includes a housing having areas or receptacles (not shown) that receive and hold physical microphones (e.g., $O_1$, $O_2$ and/or $O_3$ as described above). The headset 1100 is generally a device that can be worn by a speaker 1102, for example, a headset or earpiece that positions or holds the microphones in the vicinity of the speaker's mouth. The headset 1100 of an embodiment places a first physical microphone (e.g., physical microphone $O_1$) in a vicinity of a speaker's lips. A second physical microphone (e.g., physical microphone $O_2$) is placed a distance behind the first physical microphone. The distance of an embodiment is in a range of a few centimeters behind the first physical microphone or as described herein.

Figure 12:
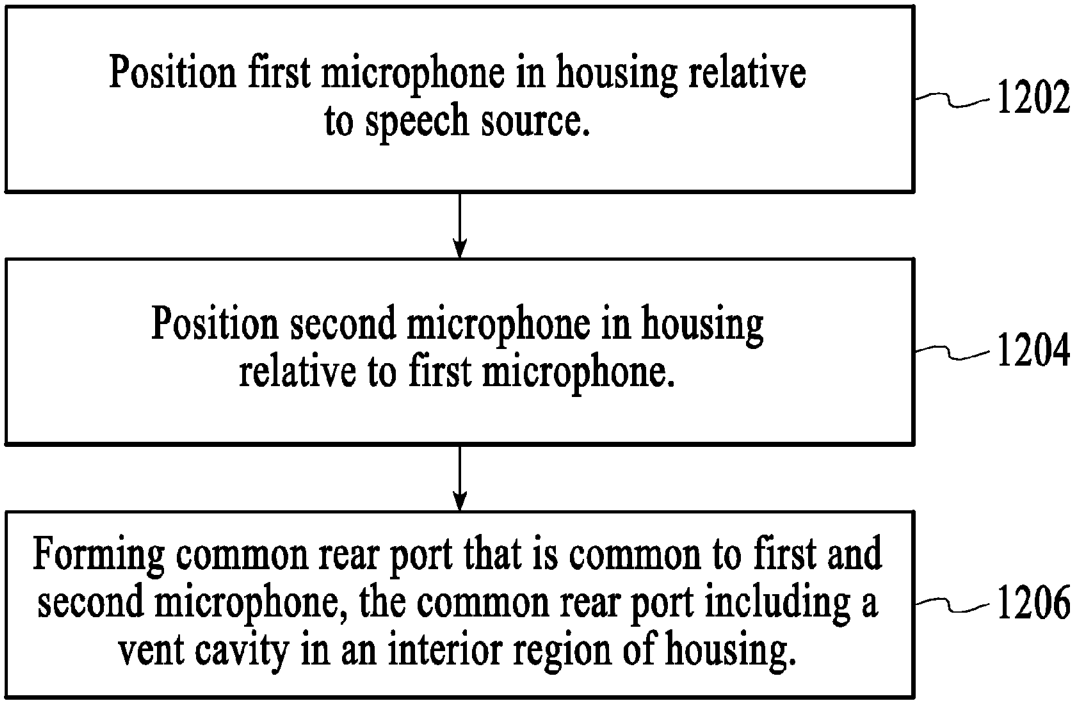
FIG. 12 is a flow diagram for forming the MA having the physical shared-vent configuration, under an embodiment.

FIG. 12 is a flow diagram for forming 1200 the MA having the physical shared-vent configuration, under an embodiment. Formation 1200 of the MA includes positioning 1202 a first microphone in a housing relative to a speech source. A second microphone is positioned 1204 in the housing relative to the first microphone. The relative positions of the first and second microphones are not restricted, but best performance was observed when the front of the first microphone was approximately orthogonal to the front of the second microphone. Formation 1200 of the MA continues with formation 1206 of a common rear port that is common to the first microphone and the second microphone. The common rear port is formed using a vent cavity in an interior region of the housing. Formation of the vent cavity comprises forming a volume that is small relative to a wavelength of acoustic signals received by the first and second microphones. The vent cavity is connected to the rear ports of each of the first microphone and the second microphone.

Figure 13:
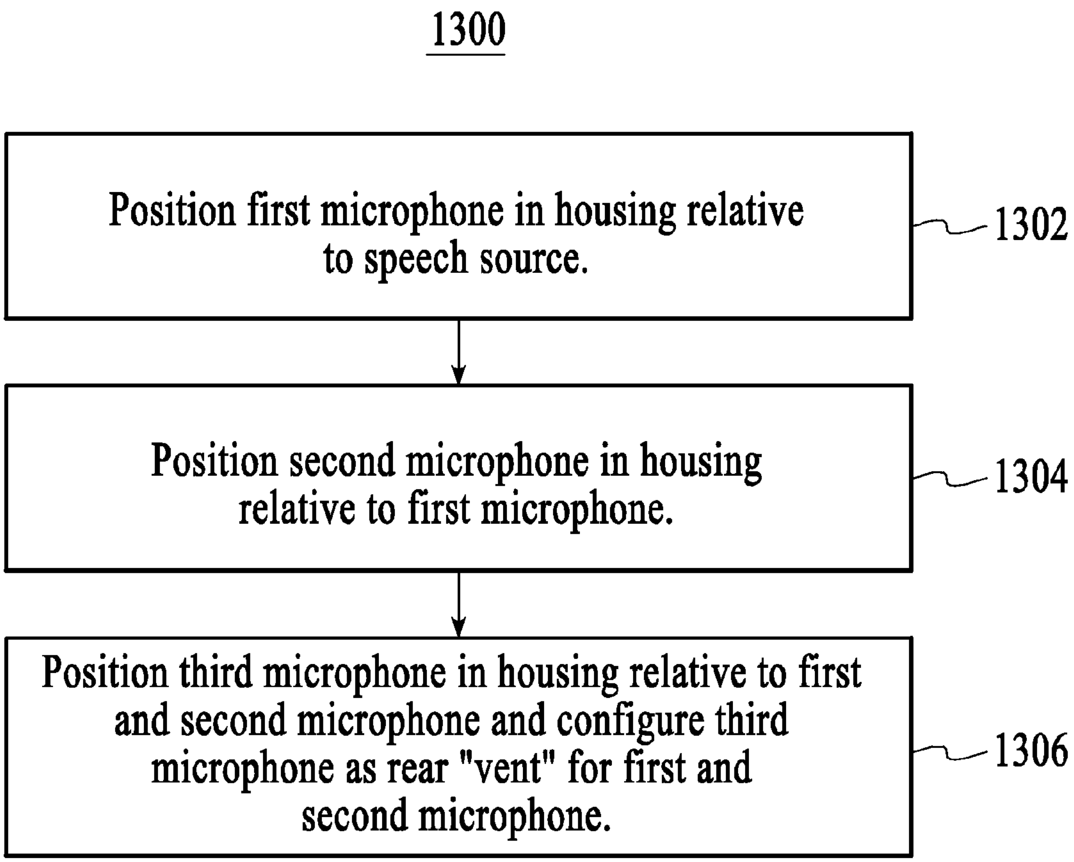
FIG. 13 is a flow diagram for forming the MA having the shared-vent configuration including omnidirectional microphones to form VDMs, under an alternative embodiment.

FIG. 13 is a flow diagram for forming 1300 the MA having the shared-vent configuration including omnidirectional microphones to form VDMs, under an alternative embodiment. Formation 1300 of the MA includes positioning 1302 a first microphone in a housing relative to a speech source. A second microphone is positioned 1304 in the housing relative to the first microphone. A third microphone is positioned 1306 in the housing relative to the first and second microphone. Best performance was observed when the relative positions of the microphones were such that the third microphone was positioned between the first and second microphones. Furthermore, in an embodiment, a front of the first microphone is approximately orthogonal to the front of each of the second and third microphones, but this is not so required. The third microphone is configured as the rear "vent" for the first and second microphones.

Figure 14:
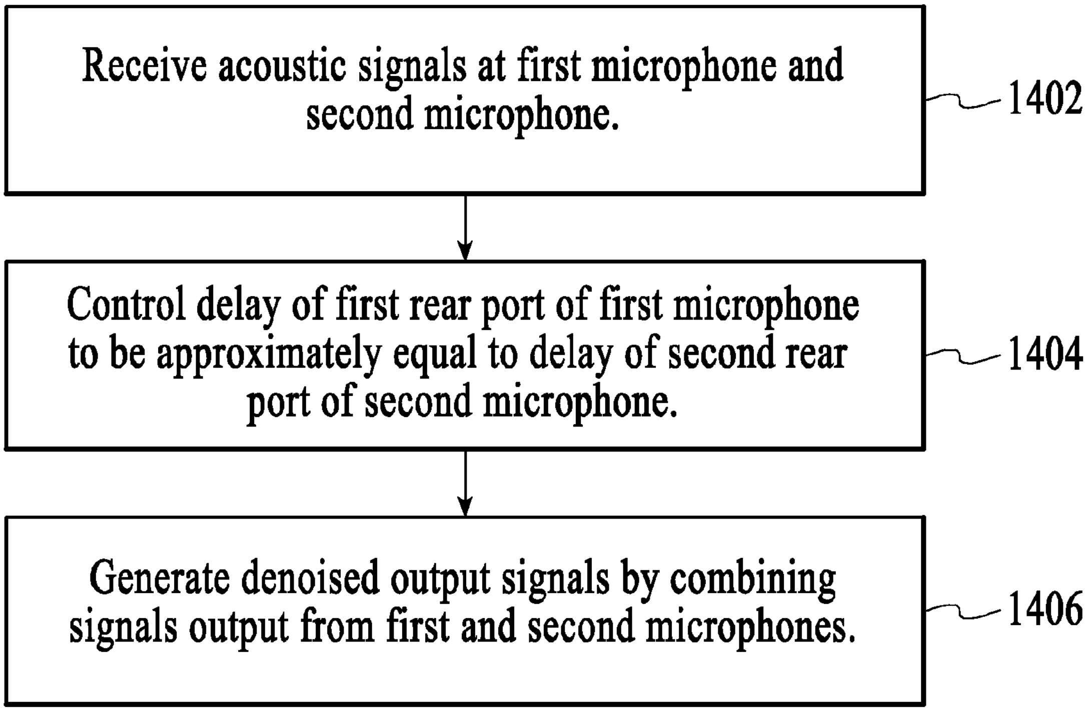
FIG. 14 is a flow diagram for denoising acoustic signals using the MA having the physical shared-vent configuration, under an embodiment.

FIG. 14 is a flow diagram for denoising 1400 acoustic signals using the MA having the physical shared-vent configuration, under an embodiment. The denoising 1400 begins by receiving 1402 acoustic signals at a first microphone and a second microphone. The denoising includes a configuration that controls 1404 a delay of the first rear port of the first microphone to be approximately equal to a delay of a second rear port of the second microphone. Controlling of the delay includes venting the first rear port and the second rear port to a common vent cavity having a volume that is small relative to a wavelength of the acoustic signals. The denoising 1400 generates 1406 output signals by combining signals from the first microphone and the second microphone, and the output signals include less acoustic noise than the acoustic signals.

Figure 15:
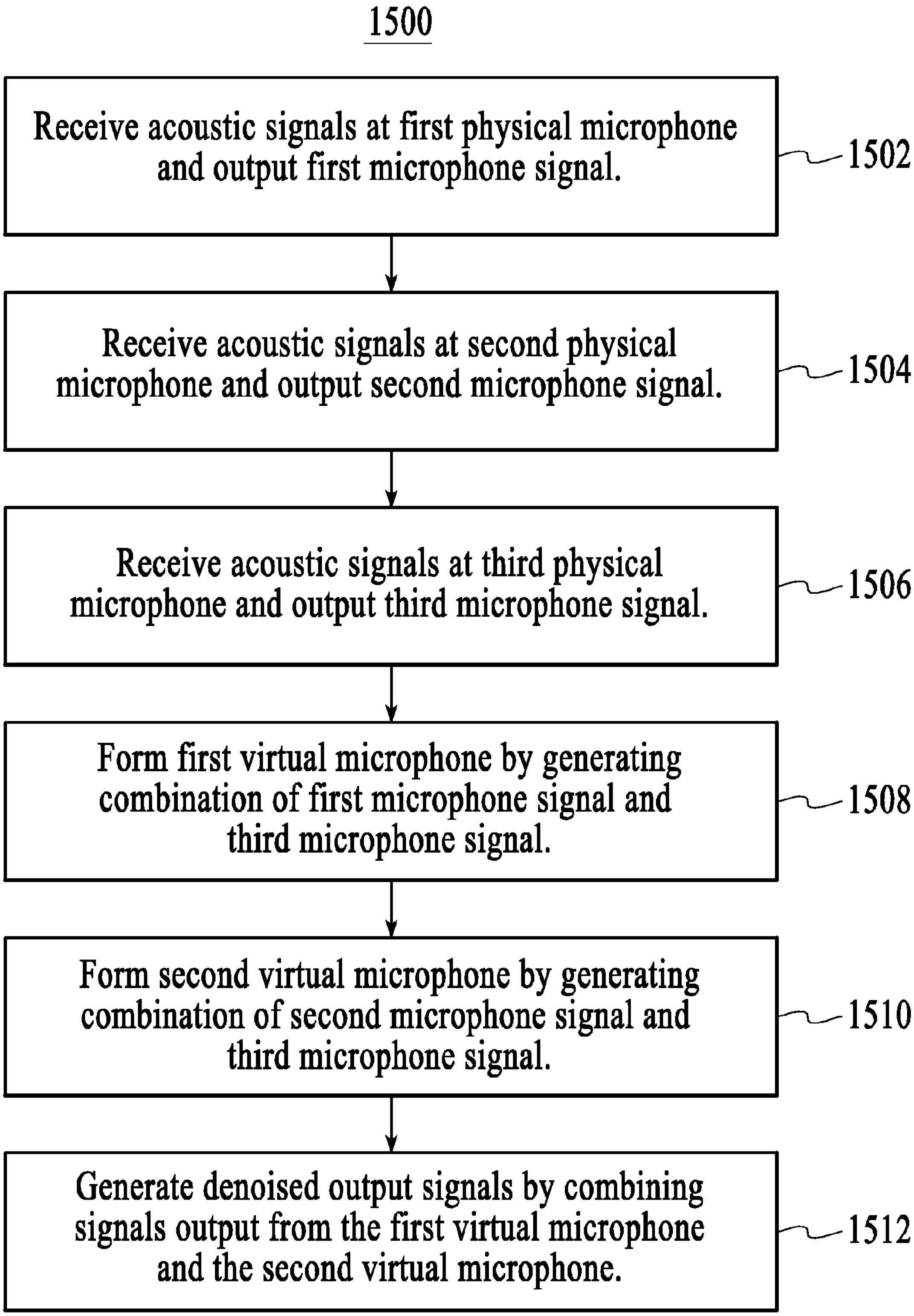
FIG. 15 is a flow diagram for denoising acoustic signals using the MA having the shared-vent configuration including omnidirectional microphones to form VDMs, under an alternative embodiment.

FIG. 15 is a flow diagram for denoising 1500 acoustic signals using the MA having the shared-vent configuration including omnidirectional microphones to form VDMs, under an alternative embodiment. The denoising 1500 begins by receiving 1502 acoustic signals at a first physical microphone and, in response to the acoustic signals, outputting a first microphone signal. The acoustic signals are received 1504 at a second physical microphone and, in response, a second microphone signal is output. The acoustic signals are received 1506 at a third physical microphone and, in response, a third microphone signal is output. A first virtual microphone is formed 1508 by generating a combination of the first microphone signal and the third microphone signal. A second virtual microphone is formed 1510 by generating a combination of the second microphone signal and the third microphone signal. The first virtual microphone and the second virtual microphone are distinct virtual directional microphones with substantially similar responses to noise and substantially dissimilar responses to speech. The denoising 1500 generates 1512 output signals by combining signals from the first virtual microphone and the second virtual microphone, and the output signals include less acoustic noise than the acoustic signals.

The construction of VMs for the adaptive noise suppression system of an embodiment includes substantially similar noise response in $V_1$ and $V_2$. Substantially similar noise response as used herein means that $H_1(z)$ is simple to model and will not change much for noises at different orientations with respect to the user, satisfying conditions R2 and R4 described above and allowing strong denoising and minimized bleedthrough.

The MA can be a component of a single system, multiple systems, and/or geographically separate systems. The MA can also be a subcomponent or subsystem of a single system, multiple systems, and/or geographically separate systems. The MA can be coupled to one or more other components (not shown) of a host system or a system coupled to the host system.

One or more components of the MA and/or a corresponding system or application to which the MA is coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, cellular telephones, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc.

The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that includes the MA can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or backend networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Embodiments of the MA described herein include a device comprising: a housing; a first microphone connected to a first side of the housing; a second microphone connected to a second side of the housing; and a vent cavity in an interior region of the housing, the vent cavity forming a common rear port of the first microphone and the second microphone and having a volume that is small relative to a wavelength of acoustic signals received by the first and second microphones.

The first microphone and the second microphone of an embodiment sample a common pressure of the vent cavity.

The first microphone and the second microphone of an embodiment have an equivalent response to the common pressure.

The device of an embodiment comprises a first orifice in a third side of the housing, the first orifice connecting the vent cavity to an external environment.

The device of an embodiment comprises a first orifice in one or more of the first side and the second side of the housing, the first orifice connecting the vent cavity to an external environment.

The device of an embodiment comprises a second orifice in a fourth side of the housing, the second orifice connecting the vent cavity to the external environment.

A first rear port of the first microphone and a second rear port of the second microphone of an embodiment are connected to the vent cavity.

A first rear port delay of the first microphone of an embodiment is approximately equal to a second rear port delay of the second microphone.

A first input to the first rear port of an embodiment is substantially similar to a second input to the second rear port.

A first front port of the first microphone and a second front port of the second microphone of an embodiment vent outside the vent cavity.

A pressure of the second front port of an embodiment is approximately proportional to a pressure of the first front port multiplied by a difference in amplitude of noise between the first and the second microphone multiplied by a delay between the first and the second microphones.

A pressure of the first rear port of an embodiment is approximately proportional to a pressure of the first front port multiplied by a difference in amplitude of noise between the first and the second microphone multiplied by a delay between the first front port and the common rear port.

A first noise response and a first speech response of the first microphone of an embodiment overlaps with a second noise response and a second speech response of the second microphone.

A first noise response of the first microphone and a second noise response of the second microphone of an embodiment are substantially similar.

A first speech response of the first microphone and a second speech response of the second microphone of an embodiment are substantially dissimilar.

The second microphone of an embodiment is positioned approximately orthogonally to the first microphone.

The second microphone of an embodiment is positioned approximately opposite to the first microphone.

The first microphone and the second microphone of an embodiment are directional microphones.

Embodiments of the MA described herein include a device comprising: a housing; a first microphone connected to a first side of the housing; a second microphone connected to a second side of the housing; and a vent cavity in an interior region of the housing, the vent cavity positioned behind the first microphone and the second microphone and having a volume that is small relative to a wavelength of acoustic signals received by the first and second microphones.

A first rear port of the first microphone and a second rear port of the second microphone of an embodiment are connected to the vent cavity and the vent cavity forms a common rear port of the first microphone and the second microphone.

The first rear port and the second rear port of an embodiment sample a common pressure of the vent cavity.

A first rear port delay of the first microphone of an embodiment is approximately equal to a second rear port delay of the second microphone.

A first delay of the first rear port of an embodiment is approximately equal to a second delay of the second rear port.

A first front port of the first microphone and a second front port of the second microphone of an embodiment vent outside the vent cavity.

A pressure of the second front port of an embodiment is approximately proportional to a pressure of the first front port multiplied by a difference in amplitude of noise between the first and the second microphone multiplied by a delay between the first and the second microphones.

A pressure of the first rear port of an embodiment is approximately proportional to a pressure of the first front port multiplied by a difference in amplitude of noise between the first and the second microphone multiplied by a delay between the first front port and the common rear port.

The device of an embodiment comprises a first orifice in a third side of the housing, the first orifice connecting the vent cavity to an external environment.

The device of an embodiment comprises a second orifice in a fourth side of the housing, the second orifice connecting the vent cavity to the external environment.

A first noise response of the first microphone and a second noise response of the second microphone of an embodiment are substantially similar.

A first speech response of the first microphone and a second speech response of the second microphone of an embodiment are substantially dissimilar.

The second microphone of an embodiment is positioned approximately orthogonally to the first microphone.

The second microphone of an embodiment is positioned approximately opposite to the first microphone.

Embodiments of the MA described herein include a device comprising: a housing; a first microphone connected to the housing; a second microphone connected to the housing; and a vent cavity in an interior region of the housing and connected to a first rear port of the first microphone and a second rear port of the second microphone, the vent cavity having a volume that is small relative to a wavelength of acoustic signals received by the first and second microphones.

Embodiments of the MA described herein include a device comprising: a housing; a first microphone connected to the housing; a second microphone connected to the housing; and a vent cavity in an interior region of the housing, the vent cavity forming a common rear port of the first microphone and the second microphone and having a volume that is small relative to a wavelength of acoustic signals received by the first and second microphones.

A first noise response of the first microphone and a second noise response of the second microphone of an embodiment are substantially similar.

A first speech response of the first microphone and a second speech response of the second microphone of an embodiment are substantially dissimilar.

The device of an embodiment comprises a plurality of vents in one or more sides of the housing, the plurality of vents connecting the vent cavity to an external environment.

Front ports of the first microphone and the second microphone of an embodiment vent outside the vent cavity.

A first rear port of the first microphone and a second rear port of the second microphone of an embodiment are connected to the vent cavity.

A rear port delay of the first microphone of an embodiment is approximately equal to a rear port delay of the second microphone.

Embodiments of the MA described herein include a device comprising: a housing; a first microphone connected to a first side of the housing; a second microphone connected to a second side of the housing, wherein the second microphone is positioned approximately orthogonally to the first microphone; a vent cavity in an interior region of the housing, the vent cavity forming a common rear port of the first microphone and the second microphone and having a volume that is small relative to a wavelength of acoustic signals received by the first and second microphones; and a first orifice in a third side of the housing and a second orifice in a fourth side of the housing, the first and the second orifice connecting the vent cavity to an external environment.

Embodiments of the MA described herein include a method comprising: receiving acoustic signals; outputting microphone signals in response to receiving the acoustic signals; controlling a delay of a first rear port of a first microphone and a second rear port of a second microphone to be approximately equal by using a common rear vent that samples a common pressure source; and generating output signals by combining the microphone signals, the output signals including less acoustic noise than the acoustic signals.

Receiving acoustic signals of an embodiment comprises receiving acoustic signals at first and second microphones.

The common rear vent of an embodiment comprises a common vent cavity connected to rear ports of the first and second microphones.

The common vent cavity of an embodiment has a volume that is small relative to a wavelength of the acoustic signals.

Outputting microphone signals of an embodiment comprises outputting a first microphone output of the first microphone and a second microphone output of the second microphone.

The first microphone and the second microphone of an embodiment sample a common pressure of the vent cavity.

The first microphone and the second microphone of an embodiment have an equivalent response to the common pressure.

The method of an embodiment comprises connecting the vent cavity to an external environment.

The method of an embodiment comprises venting front ports of the first microphone and the second microphone to an external environment.

Receiving acoustic signals of an embodiment comprises receiving acoustic signals at a first, a second and a third microphone, wherein the common rear vent comprises the third microphone.

Outputting microphone signals of an embodiment comprises outputting a first virtual microphone signal by combining a first microphone output of the first microphone and a third microphone output of the third microphone.

The method of an embodiment comprises subtracting the third microphone output from the first microphone output.

The method of an embodiment comprises delaying the third microphone output of an embodiment.

Outputting microphone signals of an embodiment comprises outputting a second virtual microphone signal by combining a second microphone output of the second microphone and the third microphone output of the third microphone.

The method of an embodiment comprises subtracting the third microphone output from the second microphone output.

The method of an embodiment comprises delaying the third microphone output.

Embodiments of the MA described herein include a method comprising: receiving acoustic signals at a first microphone and a second microphone; controlling a delay of a first rear port of the first microphone to be approximately equal to a delay of a second rear port of the second microphone, wherein controlling of the delay includes venting the first rear port and the second rear port to a common vent cavity having a volume that is small relative to a wavelength of the acoustic signals; and generating output signals by combining signals from the first microphone and the second microphone, the output signals include less acoustic noise than the acoustic signals.

Outputting microphone signals of an embodiment comprises outputting a first microphone output of the first microphone and a second microphone output of the second microphone.

The first microphone and the second microphone of an embodiment sample a common pressure of the common vent cavity.

The first microphone and the second microphone of an embodiment have an equivalent response to the common pressure.

The method of an embodiment comprises connecting the common vent cavity to an external environment.

The method of an embodiment comprises venting front ports of the first microphone and the second microphone to an external environment.

Embodiments of the MA described herein include a device comprising: a headset including a housing; a loudspeaker connected to the housing; a first microphone connected to a first side of the housing; a second microphone connected to a second side of the housing; and a vent cavity in an interior region of the housing, the vent cavity forming a common rear port of the first microphone and the second microphone and having a volume that is small relative to a wavelength of acoustic signals received by the first and second microphones.

The first microphone and the second microphone of an embodiment sample a common pressure of the vent cavity.

The first microphone and the second microphone of an embodiment have an equivalent response to the common pressure.

The device of an embodiment comprises a first orifice in a third side of the housing, the first orifice connecting the vent cavity to an external environment.

The device of an embodiment comprises a second orifice in a fourth side of the housing, the second orifice connecting the vent cavity to the external environment.

A first rear port of the first microphone and a second rear port of the second microphone of an embodiment are connected to the vent cavity.

A first rear port delay of the first microphone of an embodiment is approximately equal to a second rear port delay of the second microphone.

A first input to the first rear port of an embodiment is substantially similar to a second input to the second rear port.

A first delay of the first rear port of an embodiment is approximately equal to a second delay of the second rear port.

A first front port of the first microphone and a second front port of the second microphone of an embodiment vent outside the vent cavity.

A pressure of the second front port of an embodiment is approximately proportional to a pressure of the first front port multiplied by a difference in amplitude of noise between the first and the second microphone multiplied by a delay between the first and the second microphones.

A pressure of the first rear port of an embodiment is approximately proportional to a pressure of the first front port multiplied by a difference in amplitude of noise between the first and the second microphone multiplied by a delay between the first front port and the common rear port.

A first noise response and a first speech response of the first microphone of an embodiment overlaps with a second noise response and a second speech response of the second microphone.

A first noise response of the first microphone and a second noise response of the second microphone of an embodiment are substantially similar.

A first speech response of the first microphone and a second speech response of the second microphone of an embodiment are substantially dissimilar.

The second microphone of an embodiment is positioned approximately orthogonally to the first microphone.

The second microphone of an embodiment is positioned approximately opposite to the first microphone.

The first microphone and the second microphone of an embodiment are directional microphones.

The headset of an embodiment is portable and attaches to a region of a human head.

The first microphone and the second microphone of an embodiment receive acoustic signals including acoustic speech and acoustic noise.

A source that generates the acoustic speech of an embodiment is a mouth of a human wearing the headset.

The device of an embodiment comprises a processing component coupled to the first microphone and the second microphone.

The device of an embodiment comprises a voice activity detector (VAD) coupled to the processing component, the VAD generating voice activity signals.

The device of an embodiment comprises an adaptive noise removal application coupled to the processing component, the adaptive noise removal application receiving signals from the first and second microphones and generating the output signals.

The device of an embodiment comprises a communication channel coupled to the processing component, the communication channel comprising at least one of a wireless channel, a wired channel, and a hybrid wireless/wired channel.

The device of an embodiment comprises a communication device coupled to the headset via the communication channel, the communication device comprising one or more of cellular telephones, satellite telephones, portable telephones, wireline telephones, Internet telephones, wireless transceivers, wireless communication radios, personal digital assistants (PDAs), and personal computers (PCs).

Embodiments of the MA described herein include a device comprising: a housing that is portable and attaches to a region of a human head; a loudspeaker connected to the housing; a first microphone connected to the housing; a second microphone connected to the housing; and a vent cavity in an interior region of the housing, the vent cavity positioned behind the first microphone and the second microphone and having a volume that is small relative to a wavelength of acoustic signals received by the first and second microphones.

A first rear port of the first microphone and a second rear port of the second microphone of an embodiment are connected to the vent cavity and the vent cavity forms a common rear port of the first microphone and the second microphone.

The first rear port and the second rear port of an embodiment sample a common pressure of the vent cavity.

A first rear port delay of the first microphone of an embodiment is approximately equal to a second rear port delay of the second microphone.

A first delay of the first rear port of an embodiment is approximately equal to a second delay of the second rear port.

A first front port of the first microphone and a second front port of the second microphone of an embodiment vent outside the vent cavity.

A pressure of the second front port of an embodiment is approximately proportional to a pressure of the first front port multiplied by a difference in amplitude of noise between the first and the second microphone multiplied by a delay between the first and the second microphones.

A pressure of the first rear port of an embodiment is approximately proportional to a pressure of the first front port multiplied by a difference in amplitude of noise between the first and the second microphone multiplied by a delay between the first front port and the common rear port.

The device of an embodiment comprises a first orifice in the housing, the first orifice connecting the vent cavity to an external environment.

The device of an embodiment comprises a second orifice in the housing, the second orifice connecting the vent cavity to the external environment.

A first noise response of the first microphone and a second noise response of the second microphone of an embodiment are substantially similar.

A first speech response of the first microphone and a second speech response of the second microphone of an embodiment are substantially dissimilar.

The device of an embodiment comprises a processing component coupled to the first microphone and the second microphone.

The device of an embodiment comprises an adaptive noise removal application coupled to the processing component, the adaptive noise removal application receiving signals from the first and second microphones and generating the output signals.

The device of an embodiment comprises a communication channel coupled to the processing component, the communication channel comprising at least one of a wireless channel, a wired channel, and a hybrid wireless/wired channel. The device of an embodiment comprises a communication device coupled to the processing component via the communication channel, the communication device comprising one or more of cellular telephones, satellite telephones, portable telephones, wireline telephones, Internet telephones, wireless transceivers, wireless communication radios, personal digital assistants (PDAs), and personal computers (PCs).

Embodiments of the MA described herein include a device comprising: a headset comprising a housing that attaches to a human head; a first microphone connected to a first side of the housing; a second microphone connected to a second side of the housing; and a vent cavity in an interior region of the housing and connected to a first rear port of the first microphone and a second rear port of the second microphone, the vent cavity having a volume that is small relative to a wavelength of acoustic signals received by the first and second microphones.

The device of an embodiment comprises a processing component coupled to the first microphone and the second microphone.

The device of an embodiment comprises an adaptive noise removal application coupled to the processing component, the adaptive noise removal application receiving signals from the first and second microphones and generating the output signals.

The device of an embodiment comprises a communication channel coupled to the processing component, the communication channel comprising at least one of a wireless channel, a wired channel, and a hybrid wireless/wired channel. The device of an embodiment comprises a communication device coupled to the processing component via the communication channel, the communication device comprising one or more of cellular telephones, satellite telephones, portable telephones, wireline telephones, Internet telephones, wireless transceivers, wireless communication radios, personal digital assistants (PDAs), and personal computers (PCs).

Embodiments of the MA described herein include a device comprising: a housing; a first microphone; a second microphone; and a third microphone, wherein the third microphone functions as a common rear vent for the first and the second microphones.

The device of an embodiment comprises a first virtual microphone comprising a combination of a first microphone signal and a third microphone signal, wherein the first microphone signal is generated by the first microphone and the third microphone signal is generated by a third microphone.

The device of an embodiment comprises a second virtual microphone comprising a combination of a second microphone signal and the third microphone signal, wherein the second microphone signal is generated by the second microphone, wherein the third physical microphone functions as a common rear vent for the first and the second virtual microphones.

A first noise response of the first virtual microphone and a second noise response of the second virtual microphone of an embodiment are substantially similar.

A first speech response of the first virtual microphone and a second speech response of the second virtual microphone of an embodiment are substantially dissimilar.

The first microphone, the second microphone, and the third microphone of an embodiment are connected to a first side of the housing.

The first microphone of an embodiment is connected to a first side of the housing, the second microphone is connected to a second side of the housing, and the third microphone is connected to a third side of the housing.

The first microphone of an embodiment is connected to a first side of the housing and the second microphone and the third microphone is connected to a second side of the housing.

The second microphone of an embodiment is positioned approximately orthogonally to the first microphone The third microphone of an embodiment is positioned approximately orthogonally to the first microphone The third microphone of an embodiment is positioned adjacent the second microphone and between the first and the second microphones.

The third microphone of an embodiment is positioned adjacent the second microphone and behind the first microphone.

A first distance between the first microphone and the third microphone of an embodiment is approximately equal to a second distance between the second microphone and the third microphone.

The first microphone, the second microphone, and the third microphone of an embodiment are omnidirectional microphones.

Embodiments of the MA described herein include a device comprising: a housing; a first microphone connected to a first side of the housing; a second microphone connected to a second side of the housing; and a third microphone connected to the second side of the housing, the third microphone coupled to the first microphone and the second microphone, wherein the third microphone functions as a common rear vent for the first and the second microphones.

Embodiments of the MA described herein include a microphone array comprising: a first virtual microphone comprising a combination of a first microphone signal and a third microphone signal, wherein the first microphone signal is generated by a first physical microphone and the third microphone signal is generated by a third physical microphone; and a second virtual microphone comprising a combination of a second microphone signal and the third microphone signal, wherein the second microphone signal is generated by a second physical microphone, wherein the third physical microphone functions as a common rear vent for the first and the second virtual microphones.

The first virtual microphone and the second virtual microphone of an embodiment are distinct virtual directional microphones with substantially similar responses to noise and substantially dissimilar responses to speech.

The first virtual microphone of an embodiment comprises the third microphone signal subtracted from the first microphone signal.

The third microphone signal of an embodiment is delayed.

The second virtual microphone of an embodiment comprises the third microphone signal subtracted from the second microphone signal.

The third microphone signal of an embodiment is delayed.

The first virtual microphone of an embodiment comprises a delayed version of the third microphone signal subtracted from the first microphone signal.

The second virtual microphone of an embodiment comprises a delayed version of the third microphone signal subtracted from the second microphone signal.

The second physical microphone of an embodiment is positioned approximately orthogonally to the first physical microphone.

The third physical microphone of an embodiment is positioned approximately orthogonally to the first physical microphone.

The third physical microphone of an embodiment is positioned adjacent the second physical microphone and between the first and the second physical microphones.

The third physical microphone of an embodiment is positioned adjacent the second physical microphone and behind the first physical microphone.

A first distance between the first physical microphone and the third physical microphone of an embodiment is approximately equal to a second distance between the second physical microphone and the third physical microphone.

A first noise response of the first physical microphone and a second noise response of the second physical microphone of an embodiment are substantially similar.

A first speech response of the first physical microphone and a second speech response of the second physical microphone of an embodiment are substantially dissimilar.

The first, second and third physical microphones of an embodiment are omnidirectional Embodiments of the MA described herein include a device comprising: a first microphone outputting a first microphone signal, a second microphone outputting a second microphone signal, and a third microphone outputting a third microphone signal; and a processing component coupled to the first, second and third microphone signals, the processing component generating a virtual microphone array comprising a first virtual microphone and a second virtual microphone, wherein the first virtual microphone comprises a combination of the first microphone signal and the third microphone signal, wherein the second virtual microphone comprises a combination of the second microphone signal and the third microphone signal, wherein the third physical microphone functions as a common rear vent for the first and the second virtual microphones, wherein the first virtual microphone and the second virtual microphone have substantially similar responses to noise and substantially dissimilar responses to speech.

The first virtual microphone of an embodiment comprises a delayed version of the third microphone signal subtracted from the first microphone signal.

The second virtual microphone of an embodiment comprises a delayed version of the third microphone signal subtracted from the second microphone signal.

The third microphone of an embodiment is positioned adjacent the second microphone and between the first and the second microphones.

The third microphone of an embodiment is positioned adjacent the second microphone and behind the first microphone.

A first distance between the first microphone and the third microphone of an embodiment is approximately equal to a second distance between the second microphone and the third microphone.

The second and the third microphones of an embodiment are positioned approximately orthogonally to the first microphone.

Embodiments of the MA described herein include a sensor comprising: a physical microphone array including a first physical microphone, a second physical microphone, and a third physical microphone, the first physical microphone outputting a first microphone signal, the second physical microphone outputting a second microphone signal, and the third physical microphone outputting a third microphone signal; and a virtual microphone array comprising a first virtual microphone and a second virtual microphone and a common rear vent, the first virtual microphone comprising a combination of the first microphone signal and the third microphone signal, the second virtual microphone comprising a combination of the second microphone signal and the third microphone signal, wherein the third physical microphone functions as the common rear vent for the first and the second virtual microphones.

Embodiments of the MA described herein include a method comprising: receiving acoustic signals at a physical microphone array and in response outputting a plurality of microphone signals from the physical microphone array; forming a virtual microphone array by generating a plurality of different signal combinations from the plurality of microphone signals, wherein a number of physical microphones of the physical microphone array is larger than a number of virtual microphones of the virtual microphone array; and generating output signals by combining signals output from the virtual microphone array, the output signals including less acoustic noise than the received acoustic signals.

Embodiments of the MA described herein include a method comprising: receiving acoustic signals at a first physical microphone and in response outputting a first microphone signal from the first physical microphone; receiving acoustic signals at a second physical microphone and in response outputting a second microphone signal from the second physical microphone; receiving acoustic signals at a third physical microphone and in response outputting a third microphone signal from the third physical microphone; forming a first virtual microphone and a second virtual microphone by generating a plurality of combinations of the first microphone signal, the second microphone signal and the third microphone signal; and generating output signals by combining signals output from the first virtual microphone and the second virtual microphone, the output signals including less acoustic noise than the received acoustic signals.

Forming the first virtual microphone of an embodiment comprises combining the first microphone signal and the third microphone signal.

The first virtual microphone of an embodiment comprises the third microphone signal subtracted from the first microphone signal.

The third microphone signal of an embodiment is delayed.

Forming the second virtual microphone of an embodiment comprises combining the second microphone signal and the third microphone signal.

The second virtual microphone of an embodiment comprises the third microphone signal subtracted from the second microphone signal.

The third microphone signal of an embodiment is delayed.

Embodiments of the MA described herein include a method comprising: receiving acoustic signals at a first physical microphone and in response outputting a first microphone signal from the first physical microphone; receiving acoustic signals at a second physical microphone and in response outputting a second microphone signal from the second physical microphone; receiving acoustic signals at a third physical microphone and in response outputting a third microphone signal from the third physical microphone; forming a first virtual microphone by generating a combination of the first microphone signal and the third microphone signal; forming a second virtual microphone by generating a combination of the second microphone signal and the third microphone signal; and generating output signals by combining signals output from the first virtual microphone and the second virtual microphone, the output signals including less acoustic noise than the received acoustic signals.

Embodiments of the MA described herein include a device comprising: a headset including a housing; a loudspeaker connected to the housing; a first microphone; a second microphone; and a third microphone, wherein the third microphone functions as a common rear vent for the first and the second microphones.

The device of an embodiment comprises a first virtual microphone comprising a combination of a first microphone signal and a third microphone signal, wherein the first microphone signal is generated by the first microphone and the third microphone signal is generated by a third microphone.

The device of an embodiment comprises a second virtual microphone comprising a combination of a second microphone signal and the third microphone signal, wherein the second microphone signal is generated by the second microphone, wherein the third physical microphone functions as a common rear vent for the first and the second virtual microphones.

A first noise response of the first virtual microphone and a second noise response of the second virtual microphone of an embodiment are substantially similar.

A first speech response of the first virtual microphone and a second speech response of the second virtual microphone of an embodiment are substantially dissimilar.

The first microphone, the second microphone, and the third microphone of an embodiment are connected to a first side of the housing.

The first microphone of an embodiment is connected to a first side of the housing, the second microphone is connected to a second side of the housing, and the third microphone is connected to a third side of the housing.

The first microphone of an embodiment is connected to a first side of the housing and the second microphone and the third microphone is connected to a second side of the housing.

The second microphone of an embodiment is positioned approximately orthogonally to the first microphone The third microphone of an embodiment is positioned approximately orthogonally to the first microphone The third microphone of an embodiment is positioned adjacent the second microphone and between the first and the second microphones.

The third microphone of an embodiment is positioned adjacent the second microphone and behind the first microphone.

A first distance of an embodiment between the first microphone and the third microphone is approximately equal to a second distance between the second microphone and the third microphone.

The first microphone, the second microphone, and the third microphone of an embodiment are omnidirectional microphones.

The headset of an embodiment is portable and attaches to a region of a human head.

The first, second and third microphones of an embodiment receive acoustic signals including acoustic speech and acoustic noise.

A source that generates the acoustic speech of an embodiment is a mouth of a human wearing the headset.

The device of an embodiment comprises a processing component coupled to the first microphone, the second microphone and the third microphone.

The device of an embodiment comprises a voice activity detector (VAD) coupled to the processing component, the VAD generating voice activity signals.

The device of an embodiment comprises an adaptive noise removal application coupled to the processing component, the adaptive noise removal application receiving signals from the first, second and third microphones and generating the output signals.

The device of an embodiment comprises a communication channel coupled to the processing component, the communication channel comprising at least one of a wireless channel, a wired channel, and a hybrid wireless/wired channel.

The device of an embodiment comprises a communication device coupled to the headset via the communication channel, the communication device comprising one or more of cellular telephones, satellite telephones, portable telephones, wireline telephones, Internet telephones, wireless transceivers, wireless communication radios, personal digital assistants (PDAs), and personal computers (PCs).

Embodiments of the MA described herein include a device comprising: a housing that is portable and attaches to a region of a human head; a loudspeaker connected to the housing; a first microphone connected to a first side of the housing; a second microphone connected to a second side of the housing; and a third microphone connected to the second side of the housing, the third microphone coupled to the first microphone and the second microphone, wherein the third microphone functions as a common rear vent for the first and the second microphones.

Embodiments of the MA described herein include a headset comprising: a housing including a loudspeaker, a first physical microphone, a second physical microphone and a third physical microphone; a first virtual microphone comprising a combination of a first microphone signal and a third microphone signal, wherein the first microphone signal is generated by the first physical microphone and the third microphone signal is generated by the third physical microphone; and a second virtual microphone comprising a combination of a second microphone signal and the third microphone signal, wherein the second microphone signal is generated by the second physical microphone, wherein the third physical microphone functions as a common rear vent for the first and the second virtual microphones.

The first virtual microphone and the second virtual microphone of an embodiment are distinct virtual directional microphones with substantially similar responses to noise and substantially dissimilar responses to speech.

The first virtual microphone of an embodiment comprises the third microphone signal subtracted from the first microphone signal.

The third microphone signal of an embodiment is delayed.

The second virtual microphone of an embodiment comprises the third microphone signal subtracted from the second microphone signal. The third microphone signal of an embodiment is delayed.

The first virtual microphone of an embodiment comprises a delayed version of the third microphone signal subtracted from the first microphone signal.

The second virtual microphone of an embodiment comprises a delayed version of the third microphone signal subtracted from the second microphone signal.

The second physical microphone of an embodiment is positioned approximately orthogonally to the first physical microphone.

The third physical microphone of an embodiment is positioned approximately orthogonally to the first physical microphone.

The third physical microphone of an embodiment is positioned adjacent the second physical microphone and between the first and the second physical microphones.

The third physical microphone of an embodiment is positioned adjacent the second physical microphone and behind the first physical microphone.

A first distance between the first physical microphone and the third physical microphone of an embodiment is approximately equal to a second distance between the second physical microphone and the third physical microphone.

A first noise response of the first physical microphone and a second noise response of the second physical microphone of an embodiment are substantially similar.

A first speech response of the first physical microphone and a second speech response of the second physical microphone of an embodiment are substantially dissimilar.

The first, second and third physical microphones of an embodiment are omnidirectional.

The first, second and third microphones of an embodiment receive acoustic signals including acoustic speech and acoustic noise.

A source that generates the acoustic speech of an embodiment is a mouth of a human wearing the headset.

The headset of an embodiment comprises a processing component coupled to the first microphone, the second microphone and the third microphone.

The headset of an embodiment comprises a voice activity detector (VAD) coupled to the processing component, the VAD generating voice activity signals.

The headset of an embodiment comprises an adaptive noise removal application coupled to the processing component, the adaptive noise removal application receiving signals from the first, second and third microphones and generating output signals that are denoised versions of the acoustic signals.

The headset of an embodiment comprises a communication channel coupled to the processing component, the communication channel comprising at least one of a wireless channel, a wired channel, and a hybrid wireless/wired channel.

The headset of an embodiment comprises a communication device coupled to the headset via the communication channel, the communication device comprising one or more of cellular telephones, satellite telephones, portable telephones, wireline telephones, Internet telephones, wireless transceivers, wireless communication radios, personal digital assistants (PDAs), and personal computers (PCs).

The housing of an embodiment is portable and attaches to a region of a human head.

Embodiments of the MA described herein include a headset comprising: a loudspeaker, a first microphone outputting a first microphone signal, a second microphone outputting a second microphone signal, and a third microphone outputting a third microphone signal; and a processing component coupled to the first, second and third microphone signals, the processing component generating a virtual microphone array comprising a first virtual microphone and a second virtual microphone, wherein the first virtual microphone comprises a combination of the first microphone signal and the third microphone signal, wherein the second virtual microphone comprises a combination of the second microphone signal and the third microphone signal, wherein the third physical microphone functions as a common rear vent for the first and the second virtual microphones, wherein the first virtual microphone and the second virtual microphone have substantially similar responses to noise and substantially dissimilar responses to speech.

The headset of an embodiment comprises a processing component coupled to the first, second and third microphones.

The headset of an embodiment comprises an adaptive noise removal application coupled to the processing component, the adaptive noise removal application receiving signals from the first, second and third microphones and generating the output signals.

The headset of an embodiment comprises a communication channel coupled to the processing component, the communication channel comprising at least one of a wireless channel, a wired channel, and a hybrid wireless/wired channel. The headset of an embodiment comprises a communication device coupled to the processing component via the communication channel, the communication device comprising one or more of cellular telephones, satellite telephones, portable telephones, wireline telephones, Internet telephones, wireless transceivers, wireless communication radios, personal digital assistants (PDAs), and personal computers (PCs).

Aspects of the MA and corresponding systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the MA and corresponding systems and methods include: microcontrollers with memory (such as electronically erasable programmable read only memory (EEPROM)), embedded microprocessors, firmware, software, etc. Furthermore, aspects of the MA and corresponding systems and methods may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words “comprise,” “comprising,” and the like are to be construed in an inclusive sense as opposed to an exclusive or exhaustive sense; that is to say, in a sense of “including, but not limited to.” Words using the singular or plural number also include the plural or singular number respectively. Additionally, the words “herein,” “here-under," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the MA and corresponding systems and methods is not intended to be exhaustive or to limit the systems and methods to the precise forms disclosed. While specific embodiments of, and examples for, the MA and corresponding systems and methods are described herein for illustrative purposes, various equivalent modifications are possible within the scope of the systems and methods, as those skilled in the relevant art will recognize. The teachings of the MA and corresponding systems and methods provided herein can be applied to other systems and methods, not only for the systems and methods described above.

The elements and acts of the various embodiments described above can be combined to provide further embodiments. These and other changes can be made to the MA and corresponding systems and methods in light of the above detailed description.

In general, in the following claims, the terms used should not be construed to limit the MA and corresponding systems and methods to the specific embodiments disclosed in the specification and the claims, but should be construed to include all systems that operate under the claims. Accordingly, the MA and corresponding systems and methods is not limited by the disclosure, but instead the scope is to be determined entirely by the claims.

While certain aspects of the MA and corresponding systems and methods are presented below in certain claim forms, the inventors contemplate the various aspects of the MA and corresponding systems and methods in any number of claim forms. Accordingly, the inventors reserve the right to add additional claims after filing the application to pursue such additional claim forms for other aspects of the MA and corresponding systems and methods.

What is claimed is:

1. A method comprising:

receiving acoustic signals;

outputting microphone signals in response to receiving the acoustic signals;

controlling a delay of a first rear port of a first microphone and a second rear port of a second microphone to be approximately equal by using a common rear vent that samples a common pressure source; and generating output signals by combining the microphone signals, the output signals including less acoustic noise than the acoustic signals;

wherein receiving acoustic signals comprises receiving acoustic signals at first and second microphones;

wherein the common rear vent comprises a common vent cavity connected to rear ports of the first and second microphones; and wherein the common vent cavity has a volume that is small relative to a wavelength of the acoustic signals.

2. The method of claim 1, wherein outputting microphone signals comprises outputting a first microphone output of the first microphone and a second microphone output of the second microphone.

3. The method of claim 1, wherein the first microphone and the second microphone sample a common pressure of the vent cavity.

4. The method of claim 3, wherein the first microphone and the second microphone have an equivalent response to the common pressure.

5. The method of claim 1, comprising connecting the vent cavity to an external environment.

6. The method of claim 1, comprising venting front ports of the first microphone and the second microphone to an external environment.

7. The method of claim 1, wherein receiving acoustic signals comprises receiving acoustic signals at a first, a second and a third microphone, wherein the common rear vent comprises the third microphone.

8. The method of claim 7, wherein outputting microphone signals comprises outputting a first virtual microphone signal by combining a first microphone output of the first microphone and a third microphone output of the third microphone.

9. The method of claim 8, comprising subtracting the third microphone output from the first microphone output.

10. The method of claim 9, wherein the third microphone output is delayed.

11. The method of claim 8, wherein outputting microphone signals comprises outputting a second virtual microphone signal by combining a second microphone output of the second microphone and the third microphone output of the third microphone.

12. The method of claim 11, comprising subtracting the third microphone output from the second microphone output.

13. The method of claim 12, wherein the third microphone output is delayed.

14. A method comprising: receiving acoustic signals at a first microphone and a second microphone; controlling a delay of a first rear port of the first microphone to be approximately equal to a delay of a second rear port of the second microphone, wherein controlling of the delay includes venting the first rear port and the second rear port to a common vent cavity having a volume that is small relative to a wavelength of the acoustic signals; and generating output signals by combining signals from the first microphone and the second microphone, the output signals include less acoustic noise than the acoustic signals;

wherein the first microphone and the second microphone sample a common pressure of the common vent cavity; and wherein the first microphone and the second microphone have an equivalent response to the common pressure.

15. The method of claim 14, wherein outputting microphone signals comprises outputting a first microphone output of the first microphone and a second microphone output of the second microphone.

16. The method of claim 14, comprising connecting the common vent cavity to an external environment.

17. The method of claim 14, comprising venting front ports of the first microphone and the second microphone to an external environment.

* * * * *